US007090857B2

(12) United States Patent
Farnow et al.

(10) Patent No.: US 7,090,857 B2
(45) Date of Patent: Aug. 15, 2006

(54) ANTIGENIC PREPARATIONS

(75) Inventors: Dieter Farnow, Ingelheim am Rhein (DE); Joachim Karle, Ruesselsheim (DE); Igor D. Poliakov, Laupheim (DE); Ludmilla G. Ivanova, Laupheim (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 10/103,133

(22) Filed: Mar. 22, 2002

(65) Prior Publication Data
US 2004/0071737 A1 Apr. 15, 2004

Related U.S. Application Data

(62) Division of application No. 09/011,018, filed as application No. PCT/EP96/03535 on Aug. 9, 1996, now Pat. No. 6,379,678.

(30) Foreign Application Priority Data
Aug. 11, 1995 (GB) .................................. 9516461.2

(51) Int. Cl.
A61K 39/00 (2006.01)
(52) U.S. Cl. ................................ 424/274.1; 424/275.1; 435/254.1; 435/255.4; 435/911; 435/922; 514/8; 514/54
(58) Field of Classification Search ............. 424/274.1, 424/275.1; 435/254.1, 255.1, 255.4, 922, 435/101, 71.1, 71.3, 911; 514/54, 8
See application file for complete search history.

(56) References Cited

U.S. PATENT DOCUMENTS

| 3,867,555 | A | * | 2/1975 | Newell et al. ................ 426/60 |
| 4,146,706 | A | | 3/1979 | Hisatsuka et al. |
| 4,368,191 | A | | 1/1983 | Sarkisov et al. |
| 4,678,748 | A | | 7/1987 | Sutka et al. |
| 5,277,904 | A | | 1/1994 | Pier |
| 6,379,678 | B1 | | 4/2002 | Farnow et al. |

FOREIGN PATENT DOCUMENTS

| EP | 0 477 231 B1 | 5/1995 |
| EP | 0 834 322 A2 | 4/1998 |
| GB | 1 570 538 | 7/1980 |
| RU | 2 020 959 C1 | 10/1994 |
| WO | WO 90/15878 A1 | 12/1990 |
| WO | WO 91/07091 A1 | 5/1991 |
| WO | WO 93/07894 A1 | 4/1993 |
| WO | WO 95/05400 A1 | 2/1995 |
| WO | WO 95/26362 A1 | 10/1995 |

OTHER PUBLICATIONS

Guarro et al, Mycopathologia 122:69-77 (1993).*
Jimenez-Barbero et al, Carb. Res. 272:121-128 (1995).*
Kawarasaki et al, Chem. Pharm. Bull. 27(9):2073-2075 (1979).*
Kitazima et al, Arch. Biochem. Biophys. 152:811-820 (1972).*
Aoki, Y., and Marcus, S., "The immunologically active substances in fungi. II. The immunological activity, especially skin-test activity, of Candida antigens," *Chemical Abstracts* 69:8969, Abstract No. 8973q, The American Chemical Society (1968).
Askenase, P.W., "Cutaneous Basophil Hypersensitivity in Contact-Sensitized Guinea Pigs. I. Transfer with Immune Serum," *J. Exp. Med. 138*:1144-1155, The Rockefeller University Press (1973).
Bishop, C.T., et al., "The Water-Soluble Polysaccharides of Dermatophytes. I. A Galactomannan from Trichophyton granulosum," *Can. J. Chem. 40*:1816-1825, Ottawa National Research Council of Canada (1962).
Bishop, C.T., et al., "The Water-Soluble Polysaccharides of Dermatophytes. IV. Galactomannans I from Trichophyton granulosum, Trichophyton interdigitale, Microsporum quinckeanum, Trichophyton rubrum, and Trichophyton schönleinii," *Can. J. Chem. 43*:30-39, Ottawa National Research Council of Canada (1965).
Boehncke, W.-H., et al., "Evidence for a Pathway Independent from 2'- Deoxyguanosine and Reversible by IL-2 by which Purine Nucleoside Phosphorylase Inhibitors Block T-Cell Proliferation," *Scand. J. Immunol. 39*:327-332, Blackwell Scientific Publication (Mar. 1994).
Boukamp, P., et al., "Normal Keratinization in a Spontaneously Immortalized Aneuploid Human Keratinocyte Cell Line," *J. Cell Biol. 106*:761-771, The Rockefeller University Press (1988).
Boukamp, P., et al., "Progressive Stages of 'Transdifferentiation' from Epidermal to Mesenchymal Phenotype Induced by MyoD1 Transfection, 5-aza-2'—deoxycytidine Treatmeant, and Selection for Reduced Cell Attachment in the Human Keratinocyte Line HaCat," *J. Cell Biol. 116*:1257-1271, The Rockefeller University Press (1992).
Büttner, M., "Principles of Paramunization. Option and Limits in Veterinary Medicine," *Comp. Immun. Microbiol. Infect. Dis. 16*:1-10, Pergamon Press, Ltd. (1993).
Gad, S.C., et al., "Development and Validation of an Alternative Dermal Sensitization Test: The Mouse Ear Swelling Test (MEST)," *Toxicol. Appl. Pharmacol. 84*:93-114, Academic Press, Inc. (1986).
Golub, E.S., "Hypersensitivity," *Immunology: A Synthesis*, Sinauer Associates, Inc., Sunderland, MA, pp. 461-479 (1987).
Grappel, S.F., et al., "Immunological Studies on Dermatophytes. IV. Chemical Structures and Serological Reactivities of Polysaccharides from *Microsporum praecox, Trichophyton ferrugineum, Trichophyton sabouraudii,* and *Trichophyton tonsurans,*" *J. Bacteriol. 97*: 23-26, American Society for Microbiology (1969).
Green III, F., and Balish, E., "Suppression of In Vitro Lymphocyte Transformation During an Experimental Dermatophyte Infection," *Infect. Immun. 26*:554-562, American Society for Microbiology (1979).

(Continued)

Primary Examiner—Francisco C. Prats
(74) Attorney, Agent, or Firm—Sterne, Kessler, Goldstein & Fox P.L.L.C.

(57) ABSTRACT

The present invention relates to antigenic preparations comprising polysaccharides and/or glycopeptides preparable from keratinophilic fungi as well as yeasts, process for the preparation of these antigenic preparations, their use as pharmaceutical substances as well as their use as vaccines, including but not limited to, the prophylaxis and treatment of allergy, as well as for modulating the immune response.

22 Claims, 6 Drawing Sheets

OTHER PUBLICATIONS

Green III, F., et al., "Cutaneous Basophil Hypersensitivity and Contact Sensitivity After Cutaneous *Trichophyton mentagrophytes* Infection," *Infect. Immun. 29*:758-767, American Society for Microbiology (1980).

Green III, F., and Balish, E., "*Trichophyton mentagrophytes* Dermatophytosis in Germfree Guinea Pigs," *J. Invest. Dermatol. 75*:476-480, The Williams & Wilkins Co. (1980).

Ryle, C.M., et al., "Density-dependent modulation of synthesis of keratins 1 and 10 in the human keratinocyte line HACAT and in *ras*-transfected tumorigenic clones," *Differentiation 40*:42-54, Springer-Verlag (1989).

Strube, W., et al., "Baypamun: New Possibilities for the Control of Infectious Diseases in Domestic Animals," *Vet. Med. Rev. 60*:3-15, Leverkusen Farbenfabriken Bayer (1989).

Wu-Yuan, C.D., and Hashimoto, T., "Architecture and Chemistry of Microconidial Walls of *Trichophyton mentagrophytes*," *J. Bacteriol. 129*:1584-1592, American Society for Microbiology (1977).

International Search Report for International Application No. PCT/EP96/03535 mailed on Nov. 18, 1996.

Dialog File 351, Accession No. 9458658, Derwent WPI English language abstract for WO 93/07894 and RU 2 020 959.

* cited by examiner

ANTIGENIC PREPARATIONS

CROSS-REFERENCE TO RELATED APPLICATIONS

This application is a divisional of application Ser. No. 09/011,018, filed on May 15, 1998, allowed, which is a 371 of PCT/EP96/03535, filed on Aug. 9, 1996, which was published under PCT Article 21(2) in English on Feb. 27, 1997, the contents of each of which are entirely incorporated by reference herein.

BACKGROUND OF THE INVENTION

1. Field of the Invention

The present invention relates to antigenic preparations comprising polysaccharides and/or glycopeptides preparable from keratinophilic fungi as well as yeasts, processes for the preparation of these antigenic preparations, their use as pharmaceutical substances as well as their use as vaccines, including but not limited to, the prophylaxis and treatment of allergy, as well as for modulating the immune response.

2. Description of Related Art

Allergy in one form or another afflicts more than 20 per cent of the human population, and the alarming increase in its prevalence, morbidity and mortality over the past decade has led to its designation as the number one environmental disease (Sutton and Gould, Nature 1993, 366, pp. 421–428). Human and animal populations are afflicted by allergy to a similar extent.

In the development of allergy, immunological reactions play a key role (Paul, William E.(Editor), Fundamental Immunology, Raven Press Books, Ltd., New York, 1984). In principle two different types of allergic reactions have been described. One is immediate type hypersensitivity (ITH), for which the maximum allergic response to the allergen is observed within minutes to hours. The second is delayed type hypersensitivity (DTH). In case of DTH, the allergic response to the allergen usually reaches its maximum after 24 to 48 hours. Most likely ITH is mediated predominantly via the IgE pathway, whereas DTH is more complex. In the development of DTH it is likely that further cell mediated responses (i.e. B- and T-lymphocytes) are involved. For example, after transferring lymphocytes and antibodies from allergic donor animals to non-allergic recipient animals, the recipients developed DTH (Askenase, P. W. (1973), J. exp. Med., 138, pp. 1144–1155).

Because of their direct exposure to environmental antigens, tissues most afflicted by allergies are the epithelial tissues, especially the skin. For example, in the dermatological clinic, acute allergic contact dermatitis and chronic allergic contact eczema account for up to 15% of all dermatoses. Allergic asthma accounts for about 20% of all asthma cases in humans.

Allergic diseases that can be classified as ITH, are for example atopic eczema, allergic bronchial asthma, hay fever, rhinitis, conjunctivitis. These can develop into chronic forms as well and should not be considered exclusively as IgE-dependent reactions. Examples of DTH are acute allergic contact dermatitis and chronic allergic contact eczema, which can further be classified as DTH (type IV) with epidermal involvement. Such a patient would have previously been sensitised through contact with an allergen and has developed hypersensitivity. Renewed contact with the allergen results in acute, sub-acute or chronic inflammatory contact dermatitis.

One example for an allergic dermatitis from the veterinary clinic is Summer Eczema, also called Sweet or Queens land Itch. Summer Eczema is an allergic dermatitis of horses, belonging to the atopic form of allergic diseases (involving Type I and IV reactions). Summer Eczema is provoked by the bite of midges of the families Culicidae and Ceratopgonidae, and characterised by skin lesions with permanent erosions and exudations, mainly in regions of the mane, tail, and abdomen. Afflicted animals display a strong sensitivity of the skin with regard to irritations, i.e. touch, rain, wind etc., impairing their overall health and performance. As with other allergies, it is believed that the development of this disease is also influenced by nutritional factors. The symptoms of this disease are only visible from March to September, whereas the allergen induced sensitivity of the skin is observed during the whole year. Summer Eczema provides an interesting-general model system for the study of allergy and for the development of anti-allergic substances.

Many treatments for allergy have been proposed, depending on the clinical picture. For the treatment of acute allergic contact dermatitis, chronic allergic contact eczema and/or atopic eczema usually lipophilic creams comprising glucocorticosteroids, anti-microbial substances, anti-inflammatory drugs and/or calcium are used. For the treatment of Summer Eczema various compounds have been applied locally or parenterally, for example steroid preparations, insecticides, different galenic formulations, salicylates, oils or peptides isolated from micro-organisms. All of the above treatments only deal with the symptoms and not the causes of allergy.

Impaired immune response or immunodeficiency often play important roles in the development of allergy. Therefore, also immunotherapeutic methods, for example the administration of immune-stimulators like BCG, levamisol and other stimulators, have been used for the treatment of eczema, atopic eczema, skin abscesses, and also auto-immune diseases (A. M. Tschernucha (Editor), Koscha, published by Medicina in 1982, Moscow).

For the treatment of flea-allergic dermatitis, the administration of antibody derived peptides has been successfully used (British patent application No 8913737). For the treatment of atopic eczema, desensitivisation has also been used with relatively good results (A. M. Tschernucha (Editor), Koscha, published by Medicina in 1982, Moscow).

In spite of the various different approaches in treating allergy, to our knowledge, no antigenic compounds preparable from keratinophilic fungi or yeasts have been used for the treatment of allergy.

In the context of the present invention the term "soluble" or "nonsoluble" refers to the solubility in aqueous solution. The term "antigenic preparation" refers to any composition of matter that is able to elicit an antigenic or immunogenic response. The term "modulating the immune response" refers to the ability of the antigenic preparations of the present invention to stimulate or enhance the immune response, for example as demonstrated by their ability to stimulate the proliferation of lymphocytes in cell culture, (a detailed review can be found in Strube et al. (1989) Vet. Med. Rev., 60, pp. 3–15, Büttner M. (1993) Comp. Immun. Microbiol. Infect. Dis., 16, No. 1, pp. 1–10).

BRIEF SUMMARY OF THE INVENTION

It has now been surprisingly found, that antigenic preparations preparable from keratinophilic fungi or yeast can be used for the prophylaxis and treatment of allergies, as well as for modulating the immune response, particularly in mammals.

DETAILED DESCRIPTION OF THE INVENTION

Processes for preparing antigenic material from keratinophilic fungi as well as yeasts have now been developed. The antigenic preparations preparable according to these processes comprise polysaccharides and/or glycopeptides. The antigenic preparations can be used as pharmaceutical compositions as well as vaccines for the treatment of animals and humans, especially for the treatment of allergies and for modulating the immune response. It will be understood that the pharmaceutical compositions of this invention can have immunological as well as pharmacological utility.

The antigenic material of this invention may also be prepared from material derived from keratinophilic fungi or yeasts, for example from the fungal or yeast cell walls.

For the preparation of the antigenic preparations of the present invention, three different processes have been developed. According to these processes three different antigenic fractions (ASMP, ANMP or AEMP), in the following commonly referred to as "fractions", can be prepared from keratinophilic fungi as well as yeasts. Antigenic preparations comprising more than one fraction are referred to in the following as "complex preparation" or abbreviated "Complex".

Process 1: The fraction preparable according to this process consists of antigenic soluble material comprising polysaccharide and/or glycopeptides (ASMP).

Briefly this process, which is illustrated in detail in Example 1, comprises the following:

Keratinophilic fungi or yeasts are cultivated on Agar plates, for example as described in EP 0564620. One preferred medium is for example malt extract agar from Oxoid. Other media that will ensure growth of keratinophilic fungi or yeast may be used as well. The resulting fungal biomass is lifted off and treated with an aqueous solution of alkali. Preferred aqueous alkaline solutions are NaOH or KOH at preferred concentrations of 0.1–5% (w/v). Alkaline treatment is preferably at 20–150 C for up to 30 h. Following the processing under aqueous alkaline conditions, the solid and liquid phases of the preparation are separated, for is example by centrifugation, filtration or sedimentation. Preferably the separation is achieved by centrifugation, which ensures good separation of the fungal cell debris, for example at forces of about 3500 g. The treatment under aqueous alkaline conditions, as well as the separation step, may be repeated several times.

After the alkaline treatment, the resulting supernatant is treated under acidic aqueous conditions, e.g. 0.2–1.5M organic acid or 0.05–1M mineral acid. For example HCl or acetic acid can be used, preferably at pH values between pH 2.5 and pH 4.5. Preferably the treatment under aqueous acidic conditions is for 2 to 4 hours at temperatures of 4 to 8 C, whereafter separation of the solid and liquid layers takes place. The treatment under aqueous acidic conditions, as well as the separation step, may be repeated several times, preferably under conditions as above indicated. Then, the supernatant from the separation step is subject to a precipitation step. Preferably the precipitation is performed by adding a suitable organic solvent, e.g. an alcohol such as a lower alkanol to the supernatant, for example methanol or ethanol. A ratio of one volume supernatant to 2–5 volumes of alcohol will result in good-precipitation of the antigenic material. Other non-alcoholic precipitation procedures known to the person skilled in the art may be used as well, for example ammonium sulphate or other salt precipitation may result in precipitation of the antigenic material as well. The solid phase is then subject to a further separation step, preferably under conditions as described above. The resulting solid phase is recovered and if desired is dissolved in an aqueous solution, preferably in distilled water, typically 25 to 100 ml are used. Finally the ASMP preparation can be lyophilised and stored for prolonged time periods under dry conditions.

Process 2: The fraction preparable according to this process consists of antigenic nonsoluble material comprising polysaccharide and/or glycopeptides (ANMP). Briefly this process, which is illustrated in detail in Example 2, comprises the following:

Keratinophilic fungi or yeasts are cultivated on Agar plates, for example as described in EP 0564620. A preferred medium is for example malt extract agar from Oxoid. Other media that will ensure growth of keratinophilic fungi or yeast may be used as well. The resulting fungal biomass is lifted off and treated with an aqueous solution of alkali. Preferred aqueous alkaline solutions are NaOH or KOH at preferred concentrations of 0.1–5% (w/v). Alkaline treatment is preferably at 20–150 C for up to 30 h. Following the processing under aqueous alkaline conditions, the solid and liquid phases of the preparation are separated, for example, by centrifugation, filtration or sedimentation. Preferably the separation is achieved by centrifugation, which ensures good separation of the fungal cell debris, for example at forces of about 3500 g. The treatment under aqueous alkaline conditions may be repeated several times, as well as the separation step. After alkaline treatment, the solid phase is treated with mineral or organic acids. Preferably 0.2–1.5 M acetic acid or 0.05–1 M HCl are added to the solid phase for 0.5 to 3 hours at temperatures of 70 to 100 C. After acidic treatment the solid phase is washed with an aqueous solution, preferably distilled water. Advantageously the washing is repeated about five times. Finally the solid phase is suspended in distilled water.

Process 3: The fraction preparable according to this process consists of antigenic exogenous material comprising polysaccharide and/or glycopeptides (AEMP). Briefly this process, which is illustrated in detail in Example 3, comprises the following:

Keratinophilic fungi or yeasts are incubated in aqueous solution or cultivated in liquid medium for up to 240 hours (the volume of the solution or culture is here defined as primary volume PV). Distilled water can be used (see example 3. I.) as well as media described in EP 0564620. After incubation or cultivation, the fungal cells are separated, for example, by centrifugation, filtration or sedimentation, preferably by centrifugation under conditions as described above. The resulting supernatant is then lyophilised and subsequently dissolved in water. Preferably the volume of water equals 0.1 to 0.2 volumes of the primary volume (PV). The resulting solution is then subject to a precipitation step. Preferably the precipitation is performed by adding a suitable organic solvent, e.g. an alcohol such as a lower alkanol to the supernatant, for example methanol or ethanol. A ratio of one volume supernatant to 2–5 volumes of alcohol will result in good precipitation of the antigenic material. Other non-alcoholic precipitation procedures known to the person skilled in the art may be used as well, for example ammonium sulphate or other salt precipitation may result in precipitation of the antigenic material as well. The resulting precipitate is recovered and if desired is dissolved in an aqueous solvent, preferably in distilled water. Preferably 0.5 to 50 mg of the precipitate are dissolved in 1 ml of aqueous solvent. Finally the AEMP solution can be lyophilised and stored for prolonged time periods under dry conditions, preferably at 2 to 10 C.

Preferred fungal genera from which the above defined Fractions are preparable are the genera *Trichophyton, Microsporum* or *Candida*.

Preferred species are:
*Trichophyton equinum,*
*Trichophyton mentagrophytes,*
*Trichophyton sarkisovii,*
*Trichophyton verrucosum,*
*Microsporum canis,*
*Microsporum gypseum,* or
*Candida albicans.*

Preferred strains of the above referenced species are:
*Trichophyton equinum* DSM No. 7276,
*Trichophyton mentagrophytes* DSM No. 7279,
*Trichophyton sarkisovii* DSM No. 7278,
*Trichophyton verrucosum,* DSM 7277,
*Microsporum canis* DSM No. 7281,
*Microsporum canis* var. *obesum* DSM No. 7280,
*Microsporum canis* var. *distortum* DSM No. 7275,
*Microsporum gypseum* DSM No. 7274, or
*Candida albicans*, DSM No. 9656.

All above referenced strains have been deposited by the applicant at the DSM ("Deutsche Sammlung von Mikroorganismen und Zellkulturen GmbH", Mascheroder Weg 1B, D-38124 Braunschweig, Germany) under the provisions of the Budapest Treaty on the deposition of micro-organisms. All strains except *Candida albicans* DSM No. 9656 have been previously described in the USSR Patent Application No. 5006861 filed 21, Oct., 1991, and corresponding applications i.e. the published Patent Application EP 0564620, filed on 17, Oct., 1992.

Depending on the species the fractions can be obtained from, they are referred to according to the following.

Fractions derived from:
(i) *Trichophyton equinum*, are referred to as ASMP-TE, ANMP-TE, or AEMP-TE,
(ii) *Trichophyton mentagrophytes*, are referred to as ASMP-TM, ANMP-TM, or AEMP-TM,
(iii) *Trichophyton sarkisovii*, are referred to as ASMP-TS, ANMP-TS, or AEMP-TS,
(iv) *Trichophyton verrucosum*, are referred to as ASMP-TV, ANMP-TV, or AEMP-TV,
(v) *Microsporum canis*, are referred to as ASMP-MC, ANMP-MC, or AEMP-MC,
(vi) *Microsporum gypseum*, are referred to as ASMP-MG, ANMP-MG, or AEMP-MG, or
(vii) *Candida albicans*, are referred to as ASMP-CA, ANMP-CA, or AEMP-CA.

Where information with regard to the specific stgrain is given, the species abbreviation is followed by the digits of the specific DSM deposit, for example—AEMP-CA9656 refers to the AEMP fraction preparable from *Candida albicans* strain DSM No. 9656.

The Fractions preparable as defined in any one of the above described processes (1 to 3) comprise at least one single antigen preparable from at least one of the above referenced fungi. The antigenic preparations of the present invention comprise at least one of the above defined fractions or combinations thereof.

The antigenic preparations (ASMP and AEMP) as described in Examples 1 and 3:

1) comprise monosaccharides, amino acids and nucleotides, which are bound to a large extend in polymeric structures and to a smaller portion are free monomers.

2) mainly consist of the monosaccharide units: mannose galactose, glucose and xylose and others in different relative amount.

3) contain a mixture of polymeric structures formed by a significant amount of these monosaccharides. A significant part of these polymeric structures show molecular weights greater than 20 000 kD.

4) contain low amounts of free or bound amino acids.

5) contain low amounts of DNA molecules shown to be sensitive to digestion with DNase I.

NMR spectroscopy of the antigenic preparations ASMP and AEMP resulted in the NMR spectrograms presented in FIGS. 1 to 4.

The chemical shifts and signal multiplicities (summarized in Table 12) are in agreement with literature data for carbohydrates and amino acids.

For AEMP and ASMP fractions, e.g. MG 7274, TM 7279 and CA 9656, the carbohydrate signals cover a range from 3.2–5.5 ppm, the amino acid signals a region from 0.75–3.45 (without α-protons).

ASMP also shows typical signals for acetate-$CH_3$ 1.92 ppm.

The AEMP fractions show also typical signals for disacharides and amino acids. E.g. the TM 7279 spectrum shows signals for aromatic amino acids like Phenylanalanine, Tyrosine and Tryptophane in the region 7.15–7.9 ppm.

Concerning single fractions of ASMP or AEMP, concentrations of 0.1 to 50 mg/ml are preferred. Concerning single Fractions of ANMP, concentrations of 0.1 to 5% (v/v) are preferred.

Preferred embodiments of the antigenic preparations of the present invention comprise for example the following combinations of Fractions (Complexes):

Complex 1 comprises ASMP-TM, and ASMP-MG, and ASMP-CA. Preferably the concentration of each fraction is 0.1 to 50 mg/ml. A highly preferred embodiment according to Complex 1 is a combination of ASMP-TM7279, ASMP-MG7274, and ASMP-CA9656.

Complex 1.1 comprises ASMP-MG and ASMP-CA. Preferably the concentration of each fraction is 0.1 to 50 mg/ml. A highly preferred embodiment according to Complex 1.1 is a combination of ASMP-MG7274 and ASMP-CA9656.

Complex 2 comprises ANMP-TM, and ANMP-MG, and ANMP-CA. Preferably the concentration of each fraction is 0.1 to 5% (v/v). A highly preferred embodiment according to Complex 2 is a combination of ANMP-TM7279, ANMP-MG7274, and ANMP-CA9656.

Complex 3, comprises AEMP-TM, and AEMP-MG, and AEMP-CA. Preferably the concentration of each fraction is 0.1 to 50 mg/ml. A highly preferred embodiment according to Complex 3 is a combination of AEMP-TM7279, AEMP-MG7274, and AEMP-CA9656.

Complex 4 comprises ANMP and AEMP. The following combinations of fractions are preferred: (1) ANMP-CA and AEMP-TM or (2) ANMP-MG, ANMP-TM and AEMP-TM. Preferably the concentration of ANMP is 0.1 to 5% (v/v) and that of AEMP is 0.1 to 50 mg/ml. Highly preferred embodiments according to Complex 4 are the following combinations:

| 4.1 | ANMP-CA9656, and AEMP-TM7279; | 4.2 | ANMP-MG7274, and ANMP-TM7279, and AEMP-TM7279; |
|---|---|---|---|

Complex 5, comprises ANMP and ASMP. A preferred combination is ANMP-MG, and ANMP-TM, and ASMP-CA. Preferably the concentration of the individual ANMP fractions is 0.1 to 5% (v/v), and that of individual ASMP fractions is 0.1 to 50 mg/ml. Highly preferred is a combination of ANMP-MG7274, and ANMP-TM7279, and ASMP-CA9656.

Further preferred antigenic complexes according to the present invention comprise for example: ASMP and AEMP or ASMP and AEMP and ANMP at concentrations for ASMP and AEMP of 0.1–50 mg/ml and for ANMP at concentrations of 0.1 to 5% (v/v).

The antigenic preparations of the present invention can be applied together with suitable physiologically acceptable carriers that do not cause adverse physiological side effects, and include buffers, solutions or adjuvants, for example salt solutions, Lactate solutions or Ringer Solution. Preferred carriers are for example: Carrier A: aqueous solution comprising 0.85% (w/v) NaCl; Carrier B: aqueous solution comprising 5% (w/v) Glucose, 0.3% (w/v) meat extract "lab-lemco" (Oxoid), and 0.1% (w/v) yeast extract (Oxoid); Carrier C: Medium RPMI 1640 (purchased from Serva, catalogue no 12-702).

The antigenic preparations of the present invention can be applied per se or as solutions for injection, creams, sprays, aerosols, tablets and in other application forms known to the person skilled in the art. The antigenic preparations of the present invention may further provide highly efficient vaccines.

The antigenic preparations of the present invention are able to stimulate the proliferation of cells of the immune system and thereby are able to modulate the immune response. The antigenic preparations of the present invention are further able to inhibit the proliferation of human keratinocytes.

The antigenic preparations of the present invention may confer a high degree of resistance against allergic reactions, particularly of epithelial tissues, more particularly of the skin. They are of interest for preventing and curing allergy, and in our hands have not shown adverse side effects as demonstrated in vivo in laboratory animals (i.e. guinea pigs and white mice) and horses (i.e. cross-breed and Icelandic horses).

In particular, acute allergic dermatitis and skin lesions may be effectively cured without side effects by administering the antigenic preparation of the present invention, i.e. by vaccination. After intra muscular is injection(s) of the antigenic preparations of the present invention, the symptoms of allergic inflammation of the skin, itch and the sensitivity of the skin of individuals afflicted with allergic dermatitis may be abolished. Complete recovery from all allergic symptoms has been achieved within 2 to 8 weeks after the final injection and the allergen induced sensitivity of the skin to irritants was abolished. Further, within 1 to 6 weeks after the final injection itch may be abolished.

In a preferred embodiment, the antigenic preparations of the present invention provide a protection and cure for the so called Summer Eczema of horses, especially of Icelandic horses. After 1 to 3 intra muscular or intra dermal injection(s) of the antigenic preparations of the present invention, horses afflicted with Summer Eczema may be cured of or protected against Summer Eczema, preferred are complexes 1 and 1.1.

In a further preferred embodiment, the antigenic preparations of the present invention provide a protection and cure against alopecia in mammals. After 1 to 3 intra muscular or intra dermal injection(s) of the antigenic preparations of the present invention, mammals afflicted with alopecia may be cured of or protected against alopecia, preferred are Complexes 1 or 1.1.

In another preferred embodiment, the antigenic preparations of the present invention improve the hair condition and seasonal coat change of mammals. After 1 to 3 intramuscular or intradermal injections, coat condition may be significantly improved and in individuals afflicted with incomplete coat change complete change to the regular season coat may result, preferred are Complexes 1 or 1.1.

In another preferred embodiment, the antigenic preparations of the present invention provide a protection and cure against eczema. After 1 to 3 intra dermal or intramuscular injections) of or after topical treatment with the antigenic preparations of the present invention, mammals, i.e. humans, afflicted with eczema, may be cured of or protected against eczema, preferred are fractions ASMP-MG, ASMP-CA and ASMP-TM, i.e. ASMP-MG7274, ASMP-CA9656 and ASMP-TM7279 or complexes 1 and 1.1.

In a further preferred embodiment, the antigenic preparations of the present invention provide a protection and cure against neurodermitis. After topical treatment with the antigenic preparations of the present invention, mammals, i.e. humans, afflicted with neurodermitis, may be cured of or protected against neurodermitis, preferred are fractions ASMP-MG, ASMP-CA and ASMP-TM, i.e. ASMP-MG7274, ASMP-CA9656 and ASMP-TM7279 or complexes 1 and 1.1.

The antigenic preparations of the present invention may be used to treat a variety of indications such as those described in "Klinische Immunologie", Peter, H. H. (editor), publ. 1991 by Urban & Schwarzenberg, Munich, Germany, for example:
1. allergic airway diseases
    1.1. allergic rhinitis and conjunctivitis
        1.1.1. seasonal rhino-conjunctivitis
        1.1.2. perennial rhinitis
    1.2. asthma bronchiale
    1.3. status asthmaticus
    1.4. asthma of children
        1.4.1. obstructive lung disease after infectious bronchiolitis
        1.4.2. mild episodic or mild perennial asthma bronchiale
        1.4.3. strong perennial asthma bronchiale
2. allergic broncho pulmonary aspergillosis
3. food allergies
    3.1. IgE-mediated food allergy
        3.1.1. IgE-mediated food allergy of infants
        3.1.2. IgE-mediated food allergy of juveniles and adults
    3.2. IgG- and T-cell-mediated food allergies
    3.3. Intolerance to cow's milk
    3.4. Heiner-syndrome
    3.5. eosinophilic gastroenteropathy
    3.6. coeliac disease
4. Insect bite/sting allergy
5. urticaria in all its forms
    5.1. contact urticaria
    5.2. urticaria concomitant with allergic reactions 5.3. urticaria concomitant with intolerance to additives and inhibitors of prostaglandin synthesis (pseudo-allergy)

5.4. physical urticaria 5.4.1. dermatographia (urticaria factitia)

5.4.2. cholinergic and adrenergic urticaria 5.4.3. cold-induced urticaria 5.4.4. light urticaria 5.4.5. pressure urticaria 5.4.6. other rare forms of physical urticaria 5.5. urticarial vasculitis 5.6. mastocytosis and urticaria pigmentosa 5.7. urticaria concomitant with infectious diseases 5.8. urticaria concomitant with immunothyroiditis 5.9. urticaria and amyloidosis 6. angioedema 6.1. hereditary angloneuroticoedema (HANE)

6.2. acquired angioneuroticoedema 7. atopic dermatitis, atopic eczema 8. drug related allergy

TABLE 1

Properties and characteristics of *Candida albicans* DSM No. 9656

| Properties and characteristics of the strain | DSM No. 9656 | Epidemic strain No. 008 |
|---|---|---|
| Description of culture | 10-day colony on Saboraud agar is cream smooth, pasty, glistening, and elevated, with a central depression, the margin of the colony is regular, with a diameter of 18–22 mm | 10-day colony on Saboraud agar is cream smooth, pasty, and glistening, with folded segments, the margin of the colony is irregular, with a diameter of 15–18 mm |
| Morphological characteristics | spherical oval blasto-spores measure 3.5–5 × 5–8 μm, pseudo hyphae are 5–8 μm wide, hyphae are 2–3 μm wide. Chlamydospores on rice agar measure 13–16 μm in diameter | spherical oval blasto-spores measure 3.5–5 × 5–8 μm, pseudo hyphae are 5–8 μm wide, hyphae are 2–3 μm wide. Chlamydospores on rice agar measure 13–16 μm in diameter |
| Pathogenic characteristics | 30 days after intra peritoneal injection of 10–100 million fungal cells into white mice, 80% of the animals carried abdominal granulomas, no lethal effects are observed | 30 days after intra peritoneal injection of 10–100 million fungal cells into white mice, 80% of the animals carried abdominal granulomas, 40% of the animals died |

The present invention further relates to *Candida albicans* strain DSM No. 9656, which was obtained by directed selection based on stabilisation of cultural-morphological characteristics and attenuation of epidemic strain No. 008, which was isolated from a man in 1990.

The biological properties of *Candida albicans* strain DSM No. 9656 are described in Table 1.

Strain *Candida albicans* DSM No. 9656 further differs from the epidemic strain in its population stability, and morphological characteristics under long term passaging through nutrient media and lower virulence. Following the teachings for the preparation of antigenic preparations of the present invention, highly effective and safe antigenic preparations, according to the present invention, can be prepared from this strain.

One skilled in the art will readily appreciate that the present invention is well adapted to carry out the objects and attain the ends and advantages mentioned as well as those inherent therein. The compounds, procedures and techniques described herein are presently representative of preferred embodiments, are intended to be exemplary, and are not intended as limitations on the scope.

Having now generally described the present invention, the same will be more readily understood through reference to the following examples which are provided by way of illustration, and are not intended to be limiting of the present invention.

EXAMPLES

For all examples the centrifugation was performed at forces between 3000 g to 3500 g for about 30–50 min. The media were purchased from Oxoid (Unipath GmbH, Am Lippeglacis 6–8, 46483 Wesel, Germany) or Serva (Serva Feinbiochemica GmbH & Co. KG, Carl-Benz-Str. 7, 69115 Heidelberg, Germany). If not indicated otherwise, the fungi were cultivated as described in the Oxoid catalogue "5. aktualisierte deutsche Ausgabe" or in EP 0564 620. Fungus strains used for the preparation of the antigenic preparations of the present invention were obtained by selection and attenuation of fungus strains as described in N. V. Mazkevitch, 1981, "Spontannaja ismentchivost i kariologia nesovershennich gibov", published by Isdatelstwo Nauka, Moscow; and Ivanova, L. G., 1992, "Sistematika, morphologitcheskaja. charakteristika, biologitcheskii svojstva vosbuditelej dermatophitosov, obshih dlja givotnih i tcheloveka", Moscow, Library of the University of Moscow. Basic culturing techniques for mammalian cell cultures can be readily found in Doyle, Griffiths, and Newell (Eds.), Cell & Tissue Culture: Laboratory Procedures, John Wiley & Sons (1995). For the keratinocyte assays HaCaT cells were used (Boukamp et al. (1988), J. Cell Biol., 106, pp. 761–771, and Ryle et al. (1989), Differentiation, 40, pp. 42–54) isolated keratinocytes or other keratinocyte cell lines can be used as well. Horse lymphocytes were isolated and cultivated as described in Friemel, H., "Immunologische Arbeitsmethoden", published by VEB Gustav Fischer Verlag, Jena, 1984; or Paul, E., "Fundamental Immunology", published by Raven Press, New York, 1984. Radio assays were essentially performed as described in Boehncke et al., 1994, Scand. J. Immunol. 39, pp. 327–332 and references cited therein. NaOH, KOH, HCl and acetic acid were prepared as aqueous solutions. If not indicated otherwise, the term soluble refers to the solubility in aqueous solution. Physiologically acceptable carriers used in the experiments described below are in example: Carrier A: aqueous solution comprising 0.85% (w/v) NaCl; Carrier B: aqueous solution comprising 5% (w/v) Glucose, 0.3% (w/v) meat extract "lab-lemco" (Oxoid), and 0.1% (w/v) yeast extract (Oxoid); Carrier C: Medium RPMI 1640 (Serva).

Example 1

Antigenic soluble material comprising polysaccharide and/or glycopeptides (ASMP) was prepared from:

*Trichophyton mentagrophytes* (ASMP-TM), *Microsporum gypseum* (ASMP-MG) or *Candida albicans* (ASMP-CA), according to the following procedures:

Fungi were cultivated on Agar plates as described in EP 0564620. The fungal biomass was lifted off and for the production of:

I. ASMP-TM:

(i) *Trichophyton mentagrophytes* biomass was treated with 4.5% (w/v) of NaOH at about 140 C for 1 hour followed by centrifugation for 45 minutes. To the supernatant a 4M solution of acetic acid was added until a final pH of 3.5 was reached. After 2 hours the sediment was separated by centrifugation and 3 volumes of ethanol were added to 1 volume of supernatant. The sediment resulting from the alcoholic precipitation was sedimented by centrifugation and dissolved in distilled water. Finally the individual ASMP preparations were lyophilised.

(ii) *Trichophyton mentagrophytes* biomass was treated with 0.2% (w/v) of KOH at about 140° C. for 1 hour followed by centrifugation. The supernatant was treated with a 1M solution of HCl at a final pH of 3.5 for 4 hours at 4–10 C. The sediment was then separated by centrifugation and 2 volumes of ethanol were added to 1 volume of supernatant. The sediment resulting from the alcoholic precipitation was sedimented by centrifugation and dissolved in distilled water. Finally the individual ASMP preparations were lyophilised.

II. ASMP-MG, (i) *Microsporum gypseum* biomass was treated with 0.2% (w/v) of NaOH at about 140 C for 2 hours followed by centrifugation. The sediment was again treated with 0.2% (w/v) of NaOH at about 140 C for 2 hours followed by centrifugation and the procedure was repeated for a third time. The final supernatant was then treated with a 8M solution of acetic acid at a final pH of 3.5 for 3 hours at 18–20 C. The sediment was then separated by centrifugation, and 3 volumes of ethanol were added to 1 volume of supernatant. The sediment resulting from the alcoholic precipitation was sedimented by centrifugation and dissolved in distilled water. Finally the individual ASMP preparations were lyophilised.

(ii) *Microsporum gypseum* biomass was treated either with 3% (w/v) of KOH at about 75 C for 6 h followed by centrifugation. The sediment was again treated with 3% (w/v) of NaOH at about 75 C for 6 h followed by centrifugation. The final supernatant was then treated with a 0.5M solution of HCl at a final pH of 3.5 for 4 hours at 4–10 C. The sediment was then separated by centrifugation, and 3 volumes of methanol were added to 1 volume of supernatant. The sediment resulting from the alcoholic precipitation was sedimented by centrifugation and dissolved in distilled water. Finally the individual ASMP- preparations were lyophilised.

III. ASMP-CA:

(i) *Candida albicans* biomass was treated with 3.0% (w/v) of NaOH at about 75 C for 6 h followed by centrifugation. The sediment was again treated with 3.0% (w/v) of NaOH at about 75 C for 6 h followed by centrifugation. The final supernatant was then treated with a 12M solution of acetic acid at a final pH of 3.5 for 2 hours at 4–10 C. The sediment was then separated by centrifugation, and 2 volumes of methanol were added to 1 volume of supernatant. The sediment resulting from the alcoholic precipitation was sedimented by centrifugation and dissolved in distilled water. Finally the individual ASMP preparations were lyophilised.

(ii) *Candida albicans* biomass was treated with 4.5% (w/v) of KOH at about 35 C for 3 h followed by centrifugation. The sediment was again treated with 4.5% (w/v) of NaOH at about 35 C for 3 h followed by centrifugation, and the procedure was repeated for a third time. The final supernatant was then treated with a 0.25M solution of HCl at a final pH of 3.5 for 4 hours 18–20 C. The sediment was then separated by centrifugation, and 2 volumes of ethanol were added to 1 volume of supernatant. The sediment resulting from the alcoholic precipitation was sedimented by centrifugation and dissolved in distilled water. Finally the individual ASMP, preparations were lyophilised.

Example 2

Antigenic nonsoluble material comprising polysaccharide and/or glycopeptides (ANMP) was prepared from: *Trichophyton mentagrophytes* (ANMP-TM), *Microsporum gypseum* (ANMP-MG) or *Candida albicans* (ANMP-CA) according to the following procedures:

Fungi were cultivated on Agar plates as described in EP 0564620. The fungal biomass was lifted off and for the production of:

I. ANMP-TM:

(i) *Trichophyton mentagrophytes* biomass was treated with 0.2% (w/v) NaOH at about 35 C for 24 h followed by centrifugation. The sediment was treated with 0.3M acetic acid for about 3 hours at about 60 C and washed five times with distilled water. Each washing step was followed by centrifugation. The final sediment was resuspended in an aqueous solution of 0.85% (w/v) NaCl (Carrier A) to a final concentration of 0.5% (v/v) of ANMP-TM. The ANMP-TM preparation was stored as suspension at 2–10 C.

(ii) *Trichophyton mentagrophytes* biomass was treated with 0.2% (w/v) KOH at about 35 C for 24 h followed by centrifugation. The sediment was treated with 0.1 M HCl for 30 minutes at 70 C and washed five times with distilled water. Each washing step was followed by centrifugation. The final sediment was resuspended in RPMI 1640 (Carrier C) to a final concentration of 1.5% (v/v) of ANMP-TM. The ANMP-TM preparation was stored as suspension at 2–10 C.

II. ANMP-MG:

(i) *Microsporum gypseum* biomass was treated with 3% (w/v) NaOH at about 75 C for 6 h followed by centrifugation. The sediment was treated again with 3% (w/v) NaOH at about 75 C for 6 h followed by centrifugation. The resulting sediment was treated with 0.7M acetic acid for about 4 hours at 60 C and washed five times with distilled water. Each washing step was followed by centrifugation. The final sediment was resuspended in an aqueous solution comprising 5% (w/v) glucose, 0.1% (w/v) yeast extract from Oxoid, and 0.3% (w/v) meat extract "lab lemco" from Oxoid (Carrier B) to a final concentration of 2.5% (v/v) of ANMP-MG. The ANMP-MG preparation was stored as suspension at 2–10 C.

(ii) *Microsporum gypseum* biomass was treated with 3% (w/v) KOH at about 35° C. for 3 h followed by centrifugation. The sediment was treated again with 3% (w/v) KOH at about 35° C. for 3 h followed by centrifugation, and the procedure was repeated a third time. The resulting sediment was treated with 0.5M HCl for 30 minutes at 80 C and washed five times with distilled water. Each washing step was followed by centrifugation. The final sediment was resuspended in RPMI 1640 (Carrier C) to a final concentration of 2.0% (v/v) of ANMP-MG. The ANMP-MG preparation was stored as suspension at 2–10 C.

III. ANMP-CA:
(i) *Candida albicans* biomass was treated with 4.5% (w/v) NaOH at about 140 C for 2 hours followed by centrifugation. The sediment was treated again with 4.5% (w/v) NaOH at about 140 C for 2 hours followed by centrifugation, and the procedure was repeated a third time. The resulting sediment was treated with 1M acetic acid for 1 hour at 60 C and washed five times with distilled water. Each washing step was followed by centrifugation. The final sediment was resuspended in an aqueous solution of 0.85% (w/v) NaCl (Carrier A) to a final concentration of 1.5% (v/v) of ANMP-CA. The ANMP-CA preparation was stored as suspension at 2–10 C.
(ii) The *Candida albicans* biomass was treated with 4.5% (w/v) KOH at about 140 C for 2 hours followed by centrifugation. The sediment was treated again with 4.5% (w/v) NaOH at about 140 C for 2 hours, and the resulting sediment was treated with 0.1 M HCl for 30 minutes at 100 C and washed five times with distilled water. Each washing step was followed by centrifugation. The final sediment was resuspended in RPMI 1640 (Carrier C) to a final concentration of 2.5% (v/v) of ANMP-CA. The ANMP-CA preparation was stored as suspension at 2–10 C.

Example 3

Antigenic exogenous material comprising polysaccharide and/or glycopeptides (AEMP), was prepared from liquid cultures of: *Trichophyton mentagrophytes* (AEMP-TM), *Microsporum gypseum* (AEMP-MG) or *Candida albicans* (AEMP-CA). The liquid cultures were cultivated under conditions essentially as described in EP 0564620. The individual AEMP preparations were obtained according to the following procedures.

I. AEMP-TM: *Trichophyton mentagrophytes* was incubated for 240 h at 26 C in 1000 ml distilled water. Then, the culture, containing about $1.2 \times 10^8$ cells per ml, was centrifuged. The supernatant was lyophilised and dissolved in 100 ml of distilled water, 3 volumes of methanol were added and the precipitate was dissolved in aqueous solution. The supernatant was lyophilised resulting in AEMP-TM.

II. AEMP-MG: *Microsporum gypseum* was cultivated for 50 h at 28 C in 200 ml of Carrier C (RPMI 1640 medium from Serva). The culture, containing about $3 \times 10^7$ cells per ml, was centrifuged. The supernatant was lyophilised and dissolved in 20 ml of distilled water, 2 volumes of methanol were added and the precipitate was dissolved in aqueous solution. The supernatant was lyophilised resulting in AEMP-TM.

III. AEMP-CA: *Candida albicans* was cultivated for 30 h in 800 ml of Carrier B (1% (w/v) meat extract lab-lemco from Oxoid, 0.1% (w/v) yeast extract from Oxoid and 5% (w/v) dextrose) at 37 C. The culture, containing about $10^8$ cells per ml, was centrifuged. The supernatant was lyophilised and dissolved in a small amount of distilled water, 2 volumes of methanol were added and the precipitate was dissolved in aqueous solution. The supernatant was lyophilised resulting in AEMP-TM.

Example 4

The influence of different antigenic preparations on the growth of keratinocyte cell cultures (HaCaT cell cultures) was determined.

I. Antigenic fractions ASMP-TM, ANMP-TM, and AEMP-TM prepared from *Trichophyton mentagrophytes* DSM No. 7279, ASMP-MG, ANMP-MG, and AEMP-MG prepared from *Microsporum gypseum* DSM No. 7274, and ASMP-CA, ANMP-CA, and AEMP-CA prepared from *Candida albicans* DSM No. 9656 were used in different concentrations. The ANMP fractions as prepared according to Example 2 were lyophilised and resuspended in PBS (Phosphate Buffered Saline with a phosphate concentration of 6.7 mM at physiological pH of about 7.2; purchased from Serva, Catalogue No 17-516).

For cultivation 12 well tissue culture plates from Falcon (flat bottom, surface area 9.6 cm$^2$) were used. To each well, 0.15 ml keratinocyte cell suspension (HaCaT cells) of about 1 million cells per ml nutrient medium (RPMI 1640 supplemented with 10% (w/v) foetal calf serum), 2 ml of nutrient medium, and 0.02–0.1 ml antigenic fraction dissolved in PBS were added. To control wells no antigenic fraction material was added. Cultivation was performed in an incubator with 5% (v/v) $CO_2$ at a temperature of 37 C for about 48 hours until a confluent cell mono layer had developed in the control wells.

Inhibition of cell growth was determined by comparing the area size of cell sheets treated with the antigenic fractions compared to controls not treated with antigenic fractions (control=100%). The results are shown in Tables 2 and 3.

Inhibition of cell growth was observed at an ASMP-MG concentration of 0.1 mg/ml, an ASMP-TM concentration of 0.3 mg/ml, and an ASMP-CA concentration of 1 mg/ml. For ANMP (MG, TM, and CA) inhibition was observed at a concentration of 1 mg/ml. For AEMP-MG, inhibition of cell growth was observed at a concentration of 0.3 mg/ml, and for AEMP-TM and AEMP-CA at a concentration of 1 mg/ml.

Example 5

The influence of different antigenic fractions on the cell proliferation of horse lymphocytes was determined.

Antigenic fractions ASMP and AEMP of the fungal strains *T. mentagrophytes* DSM No. 7279, *M. gypseum* DSM No. 7274; and *C. albicans* DSM No. 9656 were used. A suspension of about 40 000 lymphocytes (from Icelandic horses) per ml of nutrient medium was prepared. Nutrient medium RPMI 1640 was supplemented with 10% (w/v) foetal calf serum. Cultivation of the lymphocytes was performed in 96 well U-bottom tissue culture plates (Falcon No 3077). 200 µl of cell suspension was distributed to each well and 20 µl of antigenic fraction dissolved in PBS was added. Controls were performed without addition of antigenic fraction material.

The tissue culture plates were incubated at 37 C with 5% (v/v) $CO_2$ for 72 hours. Then the nutrient medium was changed and a $H^3$-Thymidine-containing solution (1 µl per well) was added. A second cultivation step for 12 hours was performed, the culture was washed with PBS. Cell proliferation was determined by radio assay techniques as described in Boehncke et al., 1994, Scand. J. Immunol. 39, pp. 327–332. Measurement of the cell proliferation was performed by comparing the test cultures with the controls not exposed to antigenic fraction material. The control values were defined as 100%. The result is shown in Table 4. The individual antigenic fractions either had an inhibiting or stimulating effect on lymphocyte cell proliferation.

Example 6

This example illustrates typical complex preparations. The complexes (1 to 5) described in this example have been prepared from *Trichophyton mentagrophytes* DSM No. 7279, *Microsporum gypseum* DSM No. 7274 or *Candida albicans* DSM No. 9656.

I. Complex 1 comprises ASMP-TM, ASMP-MG, and ASMP-CA in a suitable carrier, in example

| Complex 1 | Concentration [mg/ml] | | |
|---|---|---|---|
| | A | B | C |
| ASMP-TM7279 | 5 | 10 | 30 |
| ASMP-MG7274 | 5 | 10 | 30 |
| ASMP-CA9656 | 5 | 10 | 30 |
| | in carrier A or B or C | in carrier A or B or C | in carrier A or B or C |

Complex 1.1 comprises ASMP-MG, and ASMP-CA in a suitable carrier, in example

| Complex 1 | Concentration [mg/ml] | | |
|---|---|---|---|
| | A | B | C |
| ASMP-MG7274 | 5 | 10 | 30 |
| ASMP-CA9656 | 5 | 10 | 30 |
| | in carrier A or B or C | in carrier A or B or C | in carrier A or B or C |

II. Complex 2 comprises ANMP-TM, ANMP-MG, and ANMP-CA in a suitable carrier, in example

| Complex 2 | Concentration [% (v/v)] | | | |
|---|---|---|---|---|
| | A | B | C | D |
| ANMP-TM7279 | 0.5 | 1.0 | 1.5 | 2.5 |
| ANMP-MG7274 | 0.5 | 1.0 | 1.5 | 2.5 |
| ANMP-CA9656 | 0.5 | 1.0 | 1.5 | 2.5 |
| | suspension in carrier A or B or C | suspension in carrier A or B or C | suspension in carrier A or B or C | suspension in carrier A or B or C |

III. Complex 3 comprises AEMP-TM, AEMP-MG, and AEMP-CA in a suitable carrier, in example

| Complex 3 | Concentration [mg/ml] | | |
|---|---|---|---|
| | A | B | C |
| AEMP-TM7279 | 5 | 10 | 30 |
| AEMP-MG7274 | 5 | 10 | 30 |
| AEMP-CA9656 | 5 | 10 | 30 |
| | in carrier A or B or C | in carrier A or B or C | in carrier A or B or C |

IV. Complex 4 comprises ANMP and AEMP in a suitable carrier, in example
(i) Complex 4.1 ANMP-CA9656 2.5% (v/v) AEMP-TM7279 7.1 mg/ml in carrier A or B or C

| (ii) Complex 4.2 | Concentration | |
|---|---|---|
| | A | B |
| ANMP-MG7274 | 2.5% (v/v) | 3.0% (v/v) |
| ANMP-TM7279 | 2.5% (v/v) | 3.0% (v/v) |
| AEMP-TM7279 | 10.5 mg/ml | 18.5 mg/ml |
| | in carrier A or B or C | in carrier A or B or C |

V. Complex 5 comprises ASMP and ANMP in a suitable carrier, in example

| Complex 5 | Concentration | |
|---|---|---|
| | A | B |
| ANMP-MG7274 | 1.75% (v/v) | 3% (v/v) |
| ANMP-TM7279 | 1.75% (v/v) | 3% (v/v) |
| ASMP-CA9656 | 15.6 mg/ml | 15.6 mg/ml |
| | in carrier A or B or C | in carrier A or B or C |

Example 7

The safety of different antigenic preparations was tested in vaccination experiments in animal model systems (white mice, guinea pigs, and horses).

Antigenic fractions were prepared as described in Examples 1 to 3 and 6 from *Trichophyton mentagrophytes* DSM No. 7279, *Microsporum gypseum* DSM No. 7274, or *Candida albicans* DSM No. 9656.

The following clinical observations concerning the condition of the vaccinated animals were made daily up to five days after each vaccination:
1. Common Condition
    appetite
    influence on locomotion
2. Local reaction
    oedema and inflammation at the injection site
    changes of the temperature at the injection site
    development of pain at the injection site
    necessity to treat the injection site with medicaments I. Antigenic preparations were injected one or two times with an interval of 10 days intra abdominally into white mice and intra abdominally and sub cutaneously into guinea pigs. The antigenic preparations, their concentrations and the results are shown in Tables 5 and 6 (A and B). The subcutaneous or intra abdominal injection of the fungal antigens as single or complex preparations mostly had no adverse effect on the general condition of the animals and a local reaction at the injection site was not observed.

II. Complex preparations of the fungal antigens as described in Example 6 (Complexes 4.1, 4.2, and 5) were each once injected intra muscular into the same horse at different locations (left and right side of the neck and in one of the chest muscles. Three different horses were vaccinated: (i) one pregnant mare, (ii) one foal, age 7–8 months, and (iii) one stallion, age: 6 years. The antigenic preparations, their concentrations and the results are shown in Table 7.

The intra muscular injection of the fungal antigens as complex preparation had no influence on the general condition of the horses and a local reaction at the injection site was not observed. These studies demonstrate the excellent safety of the antigenic preparations of the present invention.

Example 8

The influence of different antigenic preparations on the condition of skin and hairy coat was studied in white mice.

The antigenic preparations were prepared as described in Examples 1 to 3 and 6 from *Trichophyton mentagrophytes* DSM No. 7279, *Microsporum gypseum* DSM No. 7274, or *Candida albicans* DSM No. 9656.

The antigenic preparations were injected two times in an interval of 10 days intra abdominally into white mice. Observation of the condition of skin and hairy coat continued for five days. The antigenic preparations, their concentrations and the results are shown in Table 8. Injections of the antigenic preparations improved the condition of skin and hairy coat of white mice, as compared to control animal afflicted with dermatitis.

Example 9

The efficacy of three different antigenic preparations was studied by vaccination of Icelandic horses afflicted with Summer Eczema in a placebo controlled trial.

The antigenic preparations were prepared as described in Examples 1 to 3 and 6 from *T. mentagrophytes* DSM No. 7279, *M. gypseum* DSM No. 7274 and *C albicans* DSM No. 9656. A volume of 1 ml of Carrier A containing the individual antigenic preparations was injected three times intra muscularly. The interval between each injection was five days. Injections were administered alternately in the right and left side of the chest muscle. The antigenic preparations, their concentrations and the results are shown in Tables 9 and 10.

Administration of an antigenic preparation comprising ASMP-MG7274, ASMP-TM7279, and ASMP-CA9656 resulted in the complete cure of all vaccinated horses (3) four weeks after the third injection. The horses of the control group (injection of Carrier A without antigens) did not show any signs of recovery.

Example 10

The safety of three different antigenic preparations was studied by vaccination of Icelandic horses afflicted with Summer Eczema in a placebo controlled trial.

The antigenic preparations were prepared as described in Examples 1 to 3 and 6 from *T. mentagrophytes* DSM No. 7279, *M. gypseum* DSM No. 7274 and *C. albicans* DSM No. 9656. A volume of 1 ml of Carrier A containing the individual antigenic preparations was injected three times intra muscularly. The interval between each injection was five days. Injections were administered alternately in the right and left side of the chest muscles. Animals were observed for side effects during a time span of three days after each injection. The antigenic preparations, their concentrations and the results are shown in Table 11. General side effects like fever or loss of appetite were not observed. Only one of the antigenic preparations induced swelling at the injection-side. This minor side effect was observed in only one horse. No signs of pain were observed.

Example 11

The antiallergic efficacy of single fractions ASMP-TM7279, ASMP-MG7274 and ASMP-CA9656 as well as of complex 1 comprising ASMP-TM7279, ASMP-MG7274 and ASMP-CA9656 has been studied in a laboratory animal model.

Single fractions have been prepared according to example 1. Complex 1 was prepared according to examples 1 and 6.

CF-1 mice have been sensitzed following the modell and instructions of the Mouse Ear Swelling Test (Gad S C, Dimm B K, Dobbs D W, Reilly C, Walsh R D: Development and Validation of an Alternative Dermal Sensitization Test: The Mouse Ear Swelling Test (MEST). Toxicology and Applied Pharmacology 84, 93–114, 1986. This is a well known, validatet and OECD accepted test to examine allergic substances. To prove the efficacy of the complex or its single fractions for its anti allergic potency in a laboratory animal ear swelling which is caused by the allergene should be prevented. A placebo controled blind study with mice and two different allergens had been conducted:

The MEST was performed with CF-1 mice, which are most sensitive for allergenes. 6–10 week old CF-1 mice, have been prepared by shaving the abdominal skin, injecting 0,05 ml of Freund's Adjuvans and applying 100 µl of the allergene 1-chloro-2,4-dinitrocholorbenzene (DNCB) in one trial and mite allergene in another trial topically to the shaved abdominal skin from day 0 to 4. Seven days later 20 µl of the allergene had been applied topically to the test ear, the dissolving solution to the control ear. 24 and 48 h later the ear thickness have been measured. The same procedure has been carried out with the control group, which has been treated with placebo instead of the complex respectively the fractions of the complex.

Administration of single fractions ASMP-TM7279, ASMP-MG7274 and ASMP-CA9656 as well as of complex 1 comprising ASMP-TM7279, ASMP-MG7274 and ASMP-CA9656 resulted in 90% reduced ear swelling after sensitization with mite allergene and 87,5% reduced ear swelling after sensitization with DNCB 48 h following rechallenge in comparison to the control groups.

Example 12

The efficacy of a complex preparaton, comprising antigenic preparations ASMP-MG7274 and ASMP-CA9656, prepared as described in Example 1, was demonstrated by vaccination of an Icelandic horse afflicted with Summer Eczema.

Intradermal injections of a volume of 0.4 ml of Carrier A containing 0.2 mg of MG and 0.2 mg of CA for three times, with an interval of five days between each injection, resulted in the cure of the vaccinated horse three weeks after the final injection, as evidenced by significant decrease of the clinical symptoms. No side effects have been observed.

Example 13

The efficacy of an antigenic preparation prepared as described in Example 1 (ASMP) from *Microsporum gypseum* DSM No. 7274 was demonstrated by vaccination of an 41 year old man suffering from an eczema with inflammation, itching and erosions on the skin between the 4th and 5th toe.

A volume of 0.1 ml of Carrier A containing 0.4 mg of ASMP-MG7274 was injected intradermally, once only. The skin turned to normal 4–5 days after treatment.

Itching already had disappeared 24 h after injection. No severe side effects have been observed.

Example 14

The efficacy of an antigenic preparation prepared as described in Example 1 (ASMP) from *Candida albicans* DSM No. 9656 in the treatment of neurodermitis was demonstrated.

ASMP-CA9656 was mixed into a cream, using "Kamill Hand und Nagelcreme" purchased from Procter & Gamble, to a final concentration of 60 mg ASMP-CA9656/ml cream. The preparation was applied topically to a 3 year old girl suffering from neurodermitis with yellow crusts on the skin near both ears. The cream was applied topically to the defect part of skin once per day for 30 days. After this treatment the skin returned to normal. Side effects have not been observed.

Example 15

The efficacy of an antigenic preparation prepared as described in Example 1 (ASMP) from *Microsporum gypseum* DSM No. 7274 in the treatment of eczema was demonstrated.

ASMP-MG7274 was mixed into a cream, using "Kamill Hand und Nagelcreme" purchased from Procter & Gamble, to a final concentration of 60 mg ASMP-CA9656/ml cream. A 30 year old man suffering of an eczema with inflammation, erosions and itching on the ring finger was treated by topical application of the aflicted parts of the skin once per day for 30 days. This resulted in complete cure after treatment. Itching had disappeared a few days after treatment start. Side effects have not been observed.

Example 16

The efficacy of antigenic preparations, prepared as described in Example 1 (ASMP) from *Microsporum gypseum* DSM No. 7274, *Trichophyton mentagrophytes* DSM No. 7279, and *Candida albicans* DSM No. 9656, has been tested by vaccination in a 5 year old horse which had not changed the winter coat till June. A volume of 1 ml of Carrier A containing 15 mg of each antigenic preparation ASMP-MG7274, ASMP-TM7279 and ASMP-CA9656 (final concentration 45 mg ASMP/ml) was injected three times with an interval of five days intramuscularly, what resulted in complete change to regular season coat within 15 days. Side effects have not been observed.

Example 17

The efficacy of a complex antigenic preparations prepared as described in Example 1 (ASMP) from *Microsporum gypseum* DSM No. 7274, *Trichophyton mentagrophytes* DSM No. 7279, and *Candida albicans* DSM No. 9656 for the treatment of alopecia is demonstrated.

Two 7 year old horses suffering from alopecia one 3–5 and one on 7–10 different locations all over the body were treated with a vaccine containing 10 mg of each antigenic preparation ASMP-MG7274, ASMP-TM7279 and ASMP-CA9656 in 1 ml of carrier A (final concentration 30 mg/ml). The vaccine was injected three times with an interval of five days intramuscularly, what resulted in complete restitution of the coat of both horses 10 days after the last application. Side effects have not been observed.

Example 18

The efficacy of a complex antigenic preparation prepared as described in Example 1 (ASMP) from *Microsporum gypseum* DSM No. 7274, *Trichophyton mentagrophytes* DSM No. 7279, and *Candida albicans* DSM No. 9656 for the treatment of alopecia in horses is demonstrated.

A 10 year old horse suffering from alopecia on 10–12 different locations all over the body was treated with a vaccine containing 15 mg of each antigenic preparation ASMP-MG7274, ASMP-TM7279 and ASMP-CA9656 in 1 ml of carrier A (final concentration 45 mg/ml). The vaccine was injected three times with an interval of five days intramuscularly, what resulted in complete restitution of the coat 15 days after the last application. Side effects have not been observed.

Example 19

The efficacy of a complex antigenic preparation prepared as described in Example 1 (ASMP) from *Microsporum gypseum* DSM No. 7274, *Trichophyton mentagrophytes* DSM No. 7279, and *Candida albicans* DSM No. 9656 for the treatment of alopecia in dogs is demonstrated.

A 3 year old female dog suffering from alopecia on 2–3 different locations all over the body was treated with a vaccine containing 10 mg of each antigenic preparation ASMP-MG7274, ASMP-TM7279 and ASMP-CA9656 in 1 ml of carrier A (final concentration 30 mg/ml). The vaccine was injected three times with an interval of five days intramuscularly, what resulted in complete restitution of the coat 15 days after the last application. Side effects have not been observed.

Example 20

The efficacy of a complex antigenic preparation prepared as described in Example 1 (ASMP) from *Microsporum gypseum* DSM No. 7274, *Trichophyton mentagrophytes* DSM No. 7279, and *Candida albicans* DSM No. 9656 for the treatment of alopecia in dogs is demonstrated.

Two male dogs, one 5 years and one 8 years old, suffering from alopecia on 2–4 different locations all over the body were treated with a vaccine containing 15 mg of each antigenic preparation ASMP-MG7274, ASMP-TM7279 and ASMP-CA9656 in 1 ml of carrier A (final concentration 45 mg/ml). The vaccine was injected three times with an interval of five days intramuscularly, what resulted in complete restitution of the coat 30 days after the last application. Side effects have not been observed.

TABLE 2

Influence of the concentration of different antigenic fractions on the growth of keratinocyte cell cultures (HaCat cells in percent, compared to controls not exposed to antigenic fractions (confluent cell mono layer of controls = 100%)

| antigenic fraction | concentration of antigenic fraction [mg/ml] | | | | | | | | | | | | | |
|---|---|---|---|---|---|---|---|---|---|---|---|---|---|---|
| | 0.003 | 0.007 | 0.01 | 0.015 | 0.03 | 0.1 | 0.3 | 0.45 | 0.6 | 1.0 | 1.25 | 1.5 | 1.75 | 2 |
| | area covered by cells in percent compared to controls | | | | | | | | | | | | | |
| ASMP-MG7274 | 100 | 100 | 100 | 100 | 100 | 75 | 50 | 25 | 25 | 25 | 0 | 0 | 0 | 0 |
| ASMP-TM7279 | 100 | 100 | 100 | 100 | 100 | 100 | 75 | 50 | 25 | 0 | 0 | 0 | 0 | 0 |
| ASMP-CA9656 | 100 | 100 | 100 | 100 | 100 | 100 | 100 | 100 | 100 | 75 | 50 | 25 | 25 | 0 |
| ANMP-MG7274 | 100 | 100 | 100 | 100 | 100 | 100 | 100 | 100 | 100 | 75 | 75 | 50 | 25 | 0 |
| ANMP-TM7279 | 100 | 100 | 100 | 100 | 100 | 100 | 100 | 100 | 100 | 75 | 50 | 25 | 25 | 0 |
| ANMP-CA9656 | 100 | 100 | 100 | 100 | 100 | 100 | 100 | 100 | 100 | 75 | 75 | 50 | 25 | 0 |
| AEMP-MG7274 | 100 | 100 | 100 | 100 | 100 | 100 | 75 | 75 | 50 | 25 | 0 | 0 | 0 | 0 |
| AEMP-TM7279 | 100 | 100 | 100 | 100 | 100 | 100 | 100 | 100 | 100 | 75 | 75 | 50 | 25 | 0 |
| AEMP-CA9656 | 100 | 100 | 100 | 100 | 100 | 100 | 100 | 100 | 100 | 75 | 50 | 25 | 0 | 0 |

TABLE 3

Concentration of different antigenic fractions resulting in 50% growth inhibition of keratinocyte cells (HaCaT cells)

| strain | concentration of antigenic fraction [mg/ml] | | |
|---|---|---|---|
| | ASMP | ANMP | AEMP |
| MG7274 | 0.3 | 1.5 | 0.6 |
| TM7279 | 0.45 | 1.25 | 1.5 |
| CA9656 | 1.25 | 1.5 | 1.25 |

TABLE 4

Influence of different antigenic fractions on cell proliferation of horse lymphocytes

| concentration of antigenic fraction [µg/ml] | horse lymphocyte proliferation in % (controls without exposure to antigenic fractions = 100%) | | | | | |
|---|---|---|---|---|---|---|
| | ASMP-MG7274 | ASMP-TM7279 | ASMP-CA9656 | AEMP-MG7274 | AEMP-TM7279 | AEMP-CA9656 |
| 500 | 81.5 | 36.2 | 37.8 | 19.4 | 7.0 | 1.08 |
| 50 | 117 | 106.9 | 109.8 | 76.1 | 10.2 | 46.9 |
| 5 | 181 | 172.8 | 119.8 | 129.7 | 47.3 | 138.3 |
| 0.5 | 98.6 | 93.8 | 134.1 | 147.8 | 133.3 | 138.3 |
| 0.05 | 271.3 | 94.3 | 181.5 | 143.5 | 94.8 | 149.8 |
| 0.005 | 146.7 | 207.6 | 144.7 | 104.7 | 109.9 | 146.3 |

TABLE 5A

Reaction of test animals (white mice, body weight 12–14 g) after "first injection" of individual antigenic fractions

| antigenic fraction | concentration [mg/ml] or [% (v/v)] | injection volume [ml] | number of animals vaccinated | number of animals showing | | | | | |
|---|---|---|---|---|---|---|---|---|---|
| | | | | local pain | local reaction | increase of local temperature | loss of appetite | Impairment of locomotion | lethal reactions |
| ASMP-MG7274 | 10.5 mg/ml | 0.5 | 10 | 0 | 0 | 0 | 0 | 0 | 0 |
| ASMP-TM7279 | 12.5 mg/ml | 0.5 | 10 | 0 | 0 | 0 | 0 | 0 | 0 |
| ASMP-CA9656 | 15.5 mg/ml | 0.5 | 9 | 0 | 0 | 0 | 0 | 0 | 0 |

TABLE 5A-continued

Reaction of test animals (white mice, body weight 12–14 g) after "first injection" of individual antigenic fractions

| antigenic fraction | concentration [mg/ml] or [ % (v/v)] | injection volume [ml] | number of animals vaccinated | number of animals showing ||||||
|---|---|---|---|---|---|---|---|---|---|
| | | | | local pain | local reaction | increase of local temperature | loss of appetite | Impairment of locomotion | lethal reactions |
| ANMP-MG7274 | 3.3% | 0.5 | 8 | 0 | 1 | 0 | 0 | 0 | 0 |
| ANMP-TM7279 | 3.3% | 0.5 | 10 | 0 | 2 | 0 | 0 | 0 | 0 |
| ANMP-CA9656 | 3.3% | 0.5 | 10 | 0 | 1 | 0 | 0 | 0 | 0 |
| AEMP-MG7274 | 15.5 mg/ml | 0.5 | 10 | 0 | 1 | 0 | 0 | 0 | 0 |
| AEMP-TM7279 | 11.3 mg/ml | 0.5 | 10 | 0 | 1 | 0 | 0 | 0 | 0 |
| AEMP-CA9656 | 13.5 mg/ml | 0.5 | 10 | 0 | 1 | 0 | 0 | 0 | 0 |

TABLE 5B

Reaction of test animals after "first injection" of complex preparations

| complex | No | concentration [mg/ml] or [ % (v/v)] | injection volume [ml] | number of animals vaccinated | number of animals showing ||||||
|---|---|---|---|---|---|---|---|---|---|---|
| | | | | | local pain | local reaction | increase of local temperature | loss of appetite | Impairment of locomotion | lethal reactions |
| white mice (body weight 12–14 g) |||||||||||
| ANMP-MG7274 ANMP-TM7279 AEMP-TM7279 | 4.2 | 2.5% 2.5% 10.5 mg/ml | 0.5 | 10 | 0 | 0 | 0 | 0 | 0 | 0 |
| ANMP-CA9656 AEMP-TM7279 | 4.1 | 2.5% 7.1 mg/ml | 0.5 | 10 | 0 | 0 | 0 | 0 | 0 | 0 |
| ANMP-MG7274 ANMP-TM7279 ASMP-CA9656 | 5 | 1.75% 1.75% 15.6 mg/ml | 0.5 | 10 | 0 | 0 | 0 | 0 | 0 | 0 |
| Guinea pigs (body weight 150–200 g) |||||||||||
| ANMP-MG7274 ANMP-TM7279 AEMP-TM7279 | 4.2 | 2.5% 2.5% 10.5 mg/ml | 0.5 | 5 | 0 | 0 | 0 | 0 | 0 | 0 |
| ANMP-CA9656 AEMP-TM7279 | 4.1 | 2.5% 7.1 mg/ml | 0.5 | 5 | 0 | 0 | 0 | 0 | 0 | 0 |
| ANMP-MG7274 ANMP-TM7279 ASMP-CA9656 | 5 | 1.75% 1.75% 15.6 mg/ml | 0.5 | 5 | 0 | 0 | 0 | 0 | 0 | 0 |

TABLE 6A

Reaction of test animals (white mice, body weight 12–14 g) after "second injection" of individual antigenic fractions

| antigenic fraction | concentration [mg/ml] or [ % (v/v)] | injection volume [ml] | number of animals vaccinated | number of animals showing ||||||
|---|---|---|---|---|---|---|---|---|---|
| | | | | local pain | local reaction | increase of local temperature | loss of appetite | Impairment of locomotion | lethal reactions |
| ASMP-MG7274 | 10.5 mg/ml | 1.0 | 10 | 0 | 0 | 0 | 0 | 0 | 0 |
| ASMP-TM7279 | 12.5 mg/ml | 1.0 | 10 | 0 | 0 | 0 | 0 | 0 | 0 |
| ASMP-CA9656 | 15.5 mg/ml | 1.0 | 9 | 0 | 0 | 0 | 0 | 0 | 0 |
| ANMP-MG7274 | 3.3% | 0.5 | 8 | 0 | 1 | 0 | 0 | 0 | 0 |
| ANMP-TM7279 | 3.3% | 0.5 | 10 | 0 | 2 | 0 | 0 | 0 | 0 |
| ANMP-CA9656 | 3.3% | 1.0 | 10 | 0 | 1 | 0 | 0 | 0 | 0 |
| AEMP-MG7274 | 15.5 mg/ml | 0.5 | 10 | 0 | 1 | 0 | 0 | 0 | 0 |
| AEMP-TM7279 | 11.3 mg/ml | 1.0 | 10 | 0 | 1 | 0 | 0 | 0 | 0 |
| AEMP-CA9656 | 13.5 mg/ml | 0.5 | 10 | 0 | 1 | 0 | 0 | 0 | 0 |

TABLE 6B

Reaction of test animals after "second injection" of complex preparations

| complex | No | concentration [mg/ml] or [ % (v/v)] | injection volume [ml] | number of animals vaccinated | local pain | local reaction | increase of local temperature | loss of appetite | Impairment of locomotion | lethal reactions |
|---|---|---|---|---|---|---|---|---|---|---|
| | | | | number of animals showing | | | | | | |
| | | | white mice (body weight 12–14 g) | | | | | | | |
| ANMP-MG7274 | 4.2 | 2.5% | 0.5 | 10 | 0 | 0 | 0 | 0 | 0 | 0 |
| ANMP-TM7279 | | 2.5% | | | | | | | | |
| AEMP-TM7279 | | 10.5 mg/ml | | | | | | | | |
| ANMP-CA9656 | 4.1 | 2.5% | 0.5 | 10 | 0 | 0 | 0 | 0 | 0 | 0 |
| AEMP-TM7279 | | 7.1 mg/ml | | | | | | | | |
| ANMP-MG7274 | 5 | 1.75% | 0.5 | 10 | 0 | 0 | 0 | 0 | 0 | 0 |
| ANMP-TM7279 | | 1.75% | | | | | | | | |
| ASMP-CA9656 | | 15.6 mg/ml | | | | | | | | |
| | | | Guinea pigs (body weight 150–200 g) | | | | | | | |
| ANMP-MG7274 | 4.2 | 2.5% | 0.5 | 5 | 0 | 0 | 0 | 0 | 0 | 0 |
| ANMP-TM7279 | | 2.5% | | | | | | | | |
| AEMP-TM7279 | | 10.5 mg/ml | | | | | | | | |
| ANMP-CA9656 | 4.1 | 2.5% | 0.5 | 5 | 0 | 0 | 0 | 0 | 0 | 0 |
| AEMP-TM7279 | | 7.1 mg/ml | | | | | | | | |
| ANMP-MG7274 | 5 | 1.75% | 0.5 | 5 | 0 | 0 | 0 | 0 | 0 | 0 |
| ANMP-TM7279 | | 1.75% | | | | | | | | |
| ASMP-CA9656 | | 15.6 mg/ml | | | | | | | | |

TABLE 7

Reaction of horses after injection (single injection) of complex preparations (each horse received complexes No. 4.1, 4.2 and 5 at the same time in separate injections at separate locations)

| complex | No | concentration [mg/ml] or [ % (v/v)] | injection volume [ml] | number of horses vaccinated | local reactions | | number of horses with general reactions: | | | |
|---|---|---|---|---|---|---|---|---|---|---|
| | | | | | pain | oedema/ inflammation | increase of temperature | loss of appetite | Impairment of locomotion | loss of animals |
| ANMP-MG7274 | 4.2 | 3.0% | 0.5 | 3 | 0 | 0 | 0 | 0 | 0 | 0 |
| ANMP-TM7279 | | 3.0% | | | | | | | | |
| AEMP-TM7279 | | 18.5 mg/ml | | | | | | | | |
| ANMP-CA9656 | 4.1 | 3.0% | 0.5 | | 0 | 0 | | | | |
| AEMP-TM7279 | | 15.6 | | | | | | | | |
| ANMP-MG7274 | 5 | 3.0% | 0.5 | | 0 | 0 | | | | |
| ANMP-TM7279 | | 3.0% | | | | | | | | |
| ASMP-CA9656 | | 15.6 | | | | | | | | |

TABLE 8

Condition of skin and hairy coat after injection of complex antigenic preparations in white mice (body weight 12–14 g)

| complex | No | concentration [mg/ml] or [ % (v/v)] | injection [ml] first | injection [ml] second | number of animals | number of animals showing the following condition of the skin after vaccination: scaling | smooth | number of animals showing the following condition of the hairy coat after vaccination: smooth and shining | touseling and dim |
|---|---|---|---|---|---|---|---|---|---|
| ANMP-MG7274 | 4.2 | 2.5% | 0.5 | 1.0 | 2 | 0 | 2 | 2 | 0 |
| ANMP-TM7279 | | 2.5% | | | | | | | |
| AEMP-TM7279 | | 10.5 mg | | | | | | | |
| ANMP-CA9656 | 4.1 | 2.5% | 0.5 | 1.0 | 3 | 0 | 3 | 3 | 0 |
| AEMP-TM7279 | | 7.1 mg | | | | | | | |

TABLE 8-continued

Condition of skin and hairy coat after injection of complex antigenic preparations in white mice (body weight 12–14 g)

| complex | No | concentration [mg/ml] or [% (v/v)] | injection [ml] first | injection [ml] second | number of animals | number of animals showing the following condition of the skin after vaccination: scaling | number of animals showing the following condition of the skin after vaccination: smooth | number of animals showing the following condition of the hairy coat after vaccination: smooth and shining | number of animals showing the following condition of the hairy coat after vaccination: touseling and dim |
|---|---|---|---|---|---|---|---|---|---|
| ANMP-MG7274 | 5 | 1.75% | 0.5 | 1.0 | 1 | 0 | 1 | 1 | 0 |
| ANMP-TM7279 | | 1.75% | | | | | | | |
| ASMP-CA9656 | | 15.6 mg | | | | | | | |
| not vaccinated | — | — | — | — | 3 | 3 | 0 | 2 | 1 |

TABLE 9

Efficacy of vaccination with different complex preparations determined in Iceland horses afflicted with Summer Eczema

| complex | No | concentration [mg/ml] or [% (v/v)] | injection volume [ml] | number of injections | number of horse vaccinated | four weeks after third vaccination: number of horses cured from Summer Eczema | four weeks after third vaccination: number of horses not cured from Summer Eczema |
|---|---|---|---|---|---|---|---|
| ASMP-MG7274 | 1 | 10 mg/ml | 1 | 3 | 3 | 3 | 0 |
| ASMP-TM7279 | | 10 mg/ml | | | | | |
| ASMP-CA9656 | | 10 mg/ml | | | | | |
| ANMP-MG7274 | 2 | 1% | 1 | 3 | 3 | 0 | 3 |
| ANMP-TM7279 | | 1% | | | | | |
| ANMP-CA9656 | | 1% | | | | | |
| AEMP-MG7274 | 3 | 10 mg/ml | 1 | 3 | 3 | 1 | 2 |
| AEMP-TM7279 | | 10 mg/ml | | | | | |
| AEMP-CA9656 | | 10 mg/ml | | | | | |

TABLE 10

Efficacy of vaccination with different complex preparations, determined in Iceland horses afflicted with Summer Eczema

| complex | No | concentration of individual fractions [mg/ml] or [% (v/v)] | injection volume [ml] | number of injections | number of horses vaccinated | four weeks after third injection: number of horses cured from itching | four weeks after third injection: number of horses cured from eczema |
|---|---|---|---|---|---|---|---|
| ASMP-MG7274 | 1 | 10 mg/ml | 1 | 3 | 3 | 3 | 3 |
| ASMP-TM7279 | | 10 mg/ml | | | | | |
| ASMP-CA9656 | | 10 mg/ml | | | | | |
| ANMP-MG7274 | 2 | 1% | 1 | 3 | 3 | 1 | 0 |
| ANMP-TM7279 | | 1% | | | | | |
| ANMP-CA9656 | | 1% | | | | | |
| AEMP-MG7274 | 3 | 10 mg/ml | 1 | 3 | 3 | 2 | 1 |
| AEMP-TM7279 | | 10 mg/ml | | | | | |
| AEMP-CA9656 | | 10 mg/ml | | | | | |
| no antigen (Carrier A only) | — | — (control) | 1 | 3 | 3 | 0 | 0 |

TABLE 11

Safety of vaccination with different antigenic preparations
determined in Iceland horses afflicted with Summer Eczema

| complex | No | concentration [mg/ml] or [% (v/v)] | injection volume [ml] | number of injections | number of horses vaccinated | number of horses with local side effects observed 1 to 3 days after first to third injection | | number of horses with general side effect observed 1 to 3 days after first to third injection | |
|---|---|---|---|---|---|---|---|---|---|
| | | | | | | swelling | pain | fever | loss of appetite |
| ASMP-MG7274 | 1 | 10 mg/ml | 1 | 3 | 3 | 0 | 0 | 0 | 0 |
| ASMP-TM7279 | | 10 mg/ml | | | | | | | |
| ASMP-CA9656 | | 10 mg/ml | | | | | | | |
| ANMP-MG7274 | 2 | 1% | 1 | 3 | 3 | 0 | 0 | 0 | 0 |
| ANMP-TM7279 | | 1% | | | | | | | |
| ANMP-CA9656 | | 1% | | | | | | | |
| AEMP-MG7274 | 3 | 10 mg/ml | 1 | 3 | 3 | 1 | 0 | 0 | 0 |
| AEMP-TM7279 | | 10 mg/ml | | | | | | | |
| AEMP-CA9656 | | 10 mg/ml | | | | | | | |
| no antigen (Carrier A only) | — | — (control) | 1 | 3 | 3 | 0 | 0 | 0 | 0 |

TABLE 12

NMR-Spectra

| antigenic preparations | acetate (s) | douplet amino acids | triplet amino acids | multiplet carbohadrates | isolated CH2 amino acids | endstanding alcyl-CH amino acids | aryl-H amino acids |
|---|---|---|---|---|---|---|---|
| ASMP | | | | | | | |
| MG 7274/ 9-18-1 (FIG. 4) | 1.92 ppm | CH3 (d, 6.8 Hz) 1.33 ppm CH3 (d, 7.5 Hz) 1.48 ppm | CH3 (t, 7.1 Hz) 1.18 ppm | 3.2–4.3 ppm 4.9–5.4 ppm | 1.7–3.45 ppm | 0.95 ppm | |
| CA 9656/ b008 (FIG. 2) | 1.92 ppm | CH3 (d, 7.0 Hz) 1,33 ppm CH3 (d, 7.3 Hz) 1.48 ppm | CH3 (t, 7.0 Hz) 1.18 ppm | 3.4–4.6 ppm 4.9–5.24 ppm | CH2(AcB, 16 Hz) 2.7 ppm/2.5 ppm 3.28 ppm | 0.95 ppm | |
| TM 7279/ 32-m-1-5 (FIG. 3) | 1.92 ppm | CH3 (d, 7.1 Hz) 1.33 ppm CH3 (d, 7.1 Hz) 1.48 ppm | CH3 (t, 7.1 Hz) 1.18 ppm | 3.5–4.35 ppm 5.0–5.25 ppm | 2.1–3.3 ppm | 0.85–0.95 ppm | |
| AEMP | | | | | | | |
| TM 7279/ p32-5-1 (FIG. 1, A–C) | | CH3 (d, 6.5 Hz) 1.33 ppm CH3 (d, 7.5 Hz) 1.48 ppm | | 3.2–4.07 ppm CH (d, 8.2 Hz) 4.65 ppm CH (d, 4.0 Hz) 5.23 ppm | 1.6–3.12 ppm | 0.84–1.08 ppm | 7.15–7.9 ppm | ppm = part per million
s = singulet

Figure 1A:
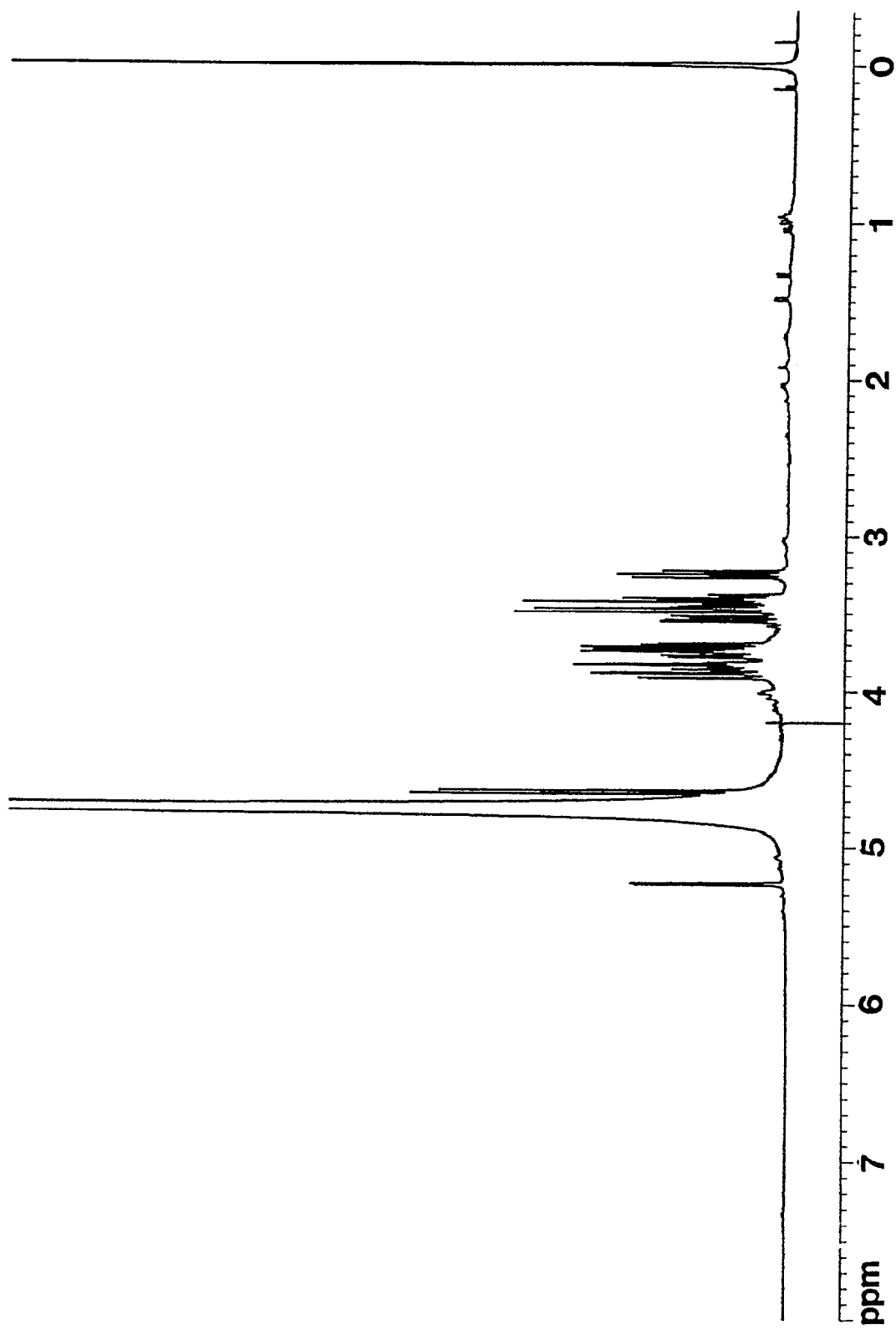
FIGS. 1 to 4.
Figure 1B:
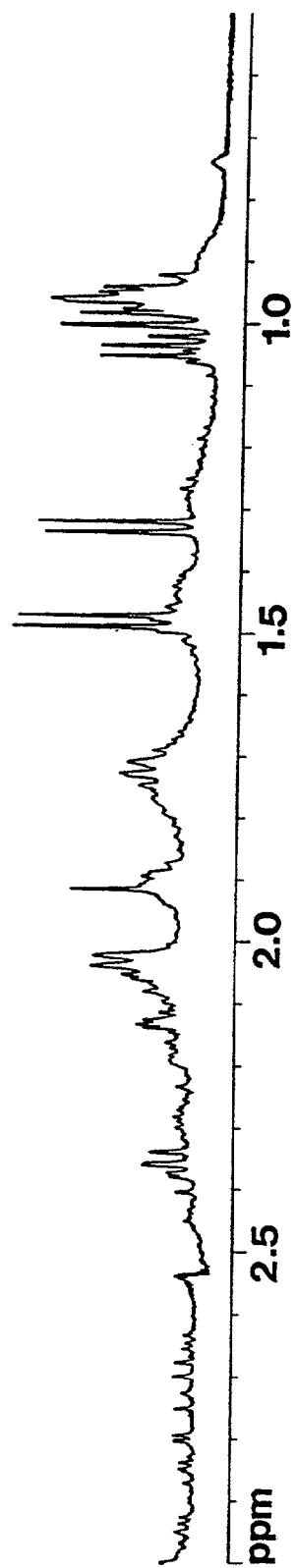
Figure 1C:
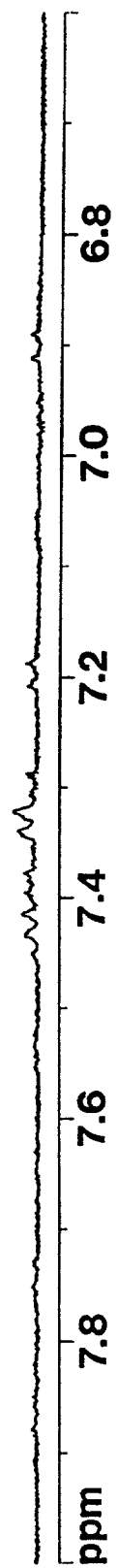
Figure 2:
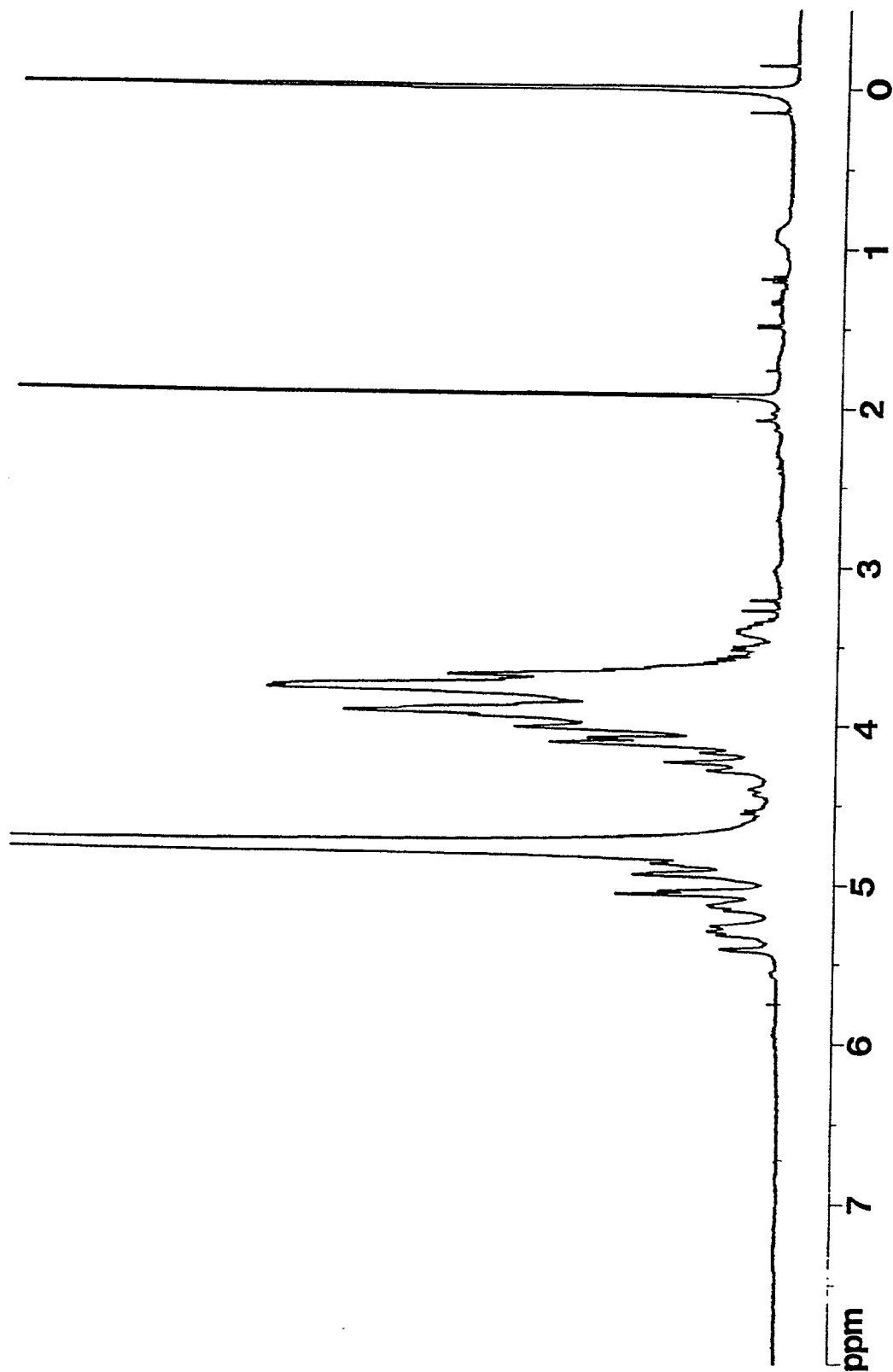
Figure 3:
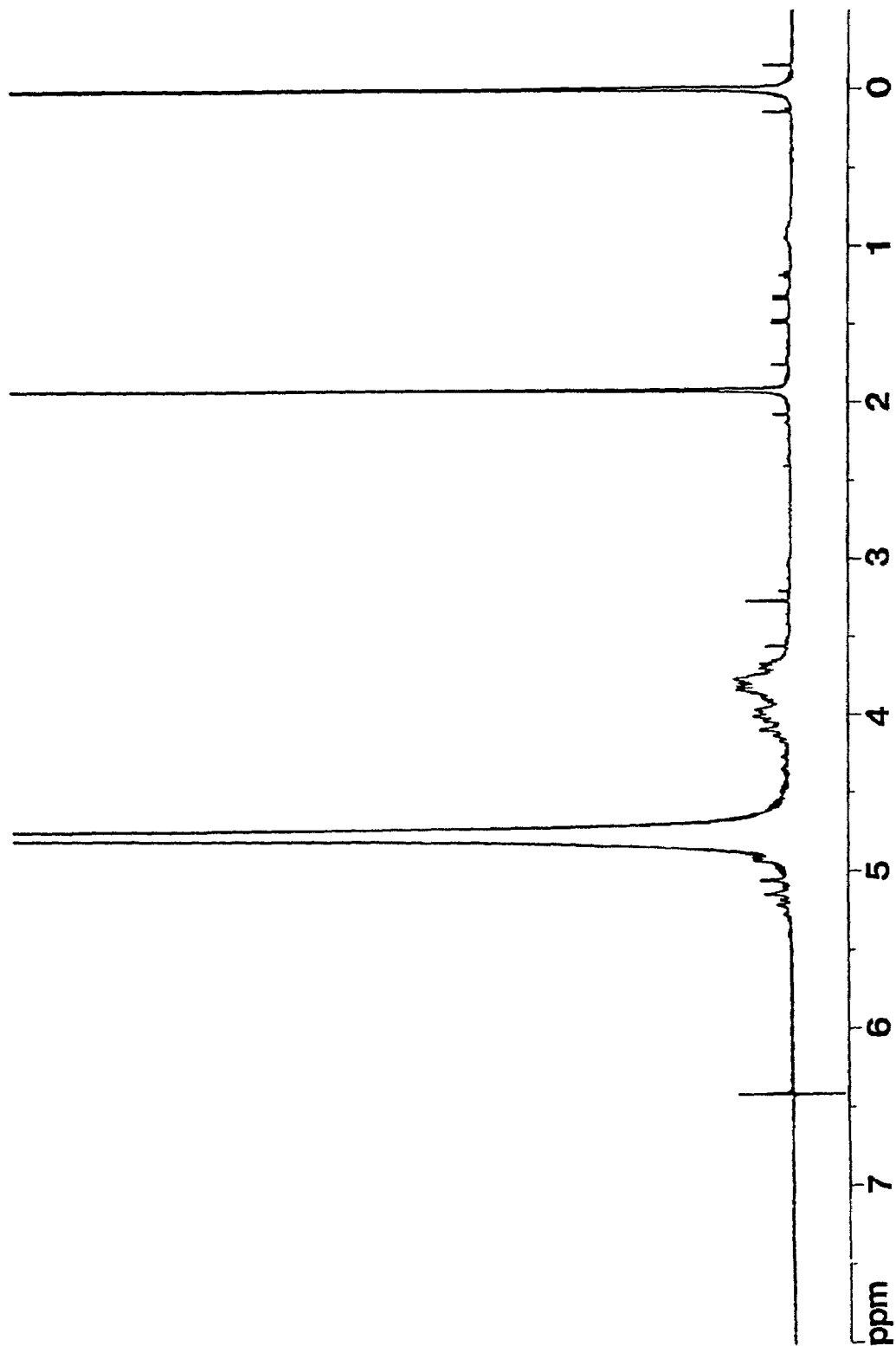
Figure 4:
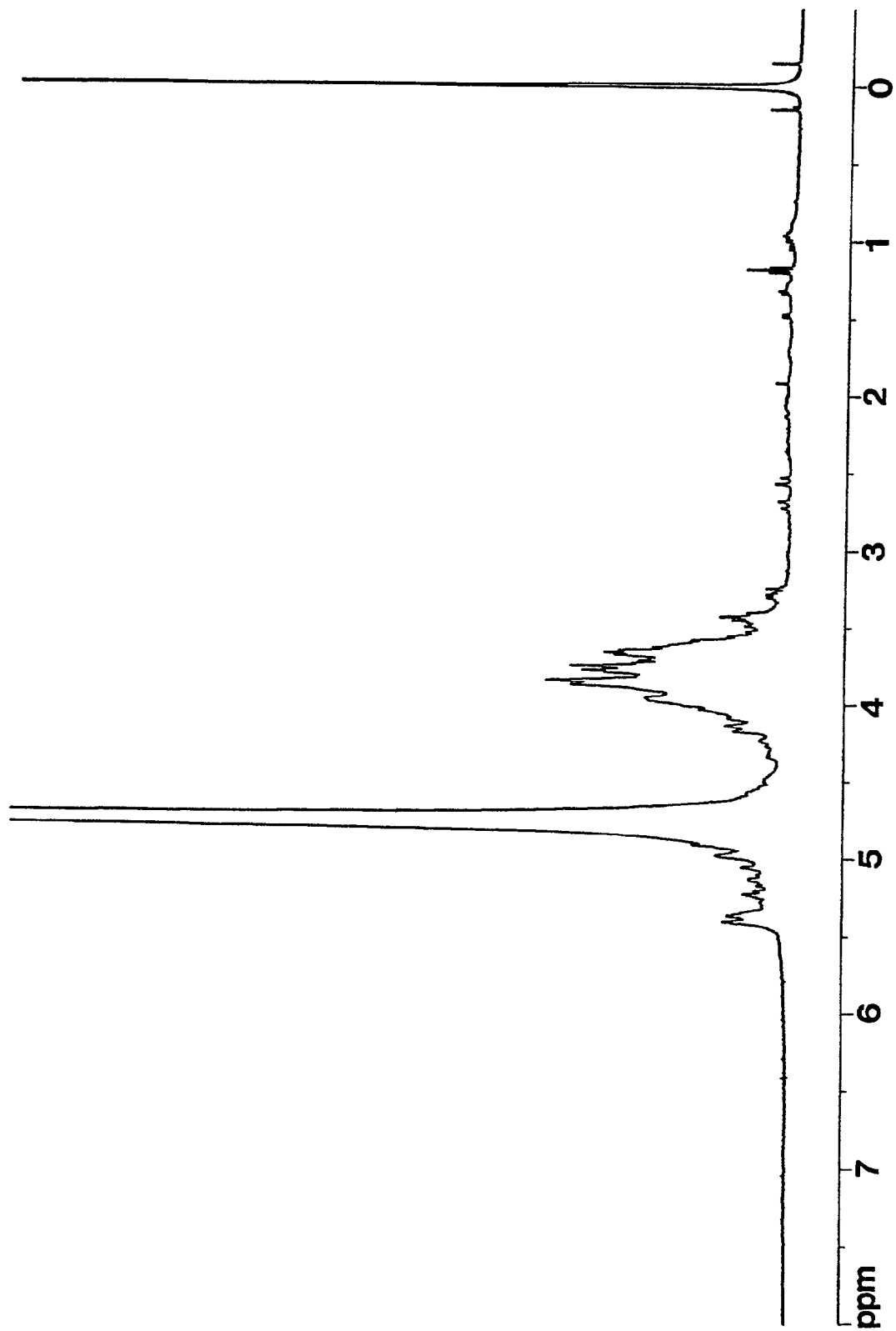

NMR experiments of ASMP and AEMP fractions as shown in FIGS. 1 to 4 were performed according to the following:

Spectra have been obtained in D$_2$O on a 250 MHZ BRUKER digital NMR-spectrometer (model DRX 400) with a $^1$H-frequency of 400.13 Mc. Sweep width is 14.5 ppm, ambient temperature is 300K. Chemical shifts are referenced by means of the solvent distance.

The standard $^1$H-one dimensional spectra have been obtained using the appropriate BRUKER pulse program.

The invention claimed is:

1. A process for the preparation of an antigenic material soluble in aqueous solutions (ASMP) which comprises at least one polysaccharide and at least one glycopeptide, said process consisting of:
   a) contacting fungal cells, which belong to keratinophilic fungi or keratinophilic yeasts, or parts thereof with an aqueous alkaline solution at about 20° C. to about 150° C., thereby obtaining a preparation;

b) separating said preparation into solid and liquid phases by centrifugation or by sedimentation, thereby obtaining a first supernatant;

c) contacting said first supernatant with mineral or organic acid and allowing solid and liquid phases to separate, thereby obtaining a second supernatant; and d) precipitating out of said second supernatant the ASMP.

2. The process as claimed in claim 1, wherein a) the fungal cells or parts thereof are contacted with KOH or NaOH of about 0.1–5% (w/v), at about 20–150° C., for up to 30 hours, thereby obtaining the preparation;

b) centrifuging said preparation, thereby obtaining the first supernatant;

c) contacting said first supernatant with 0.2–1.5M organic acid or 0.05–1M mineral acid, centrifuging, thereby obtaining a second supernatant; and d) precipitating out of said second supernatant the ASMP by contacting said second supernatant with an organic solvent or a salt.

3. The process as claimed in claim 2, wherein said organic solvent or a salt is selected from the group consisting of an alcohol, a lower alkanol and ammonium sulphate.

4. The process as claimed in claim 2, further comprising:

e) dissolving said ASMP in an aqueous solution.

5. The process according to claim 1, wherein said keratinophilic fungus is selected from a group of two fungi genera consisting of *Trichophyton* and *Microsporum*; and said yeast is in the genus *Candida*.

6. The process according to claim 1, wherein said keratinophilic fungus is selected from a group consisting of *Trichophyton equinum, Trichophyton mentagrophytes, Trichophyton sarkisovii, Trichophyton verrucosum, Microsporum canis, Microsporum gypseum,* and *Candida albicans*.

7. The process according to claim 1, wherein said keratinophilic fungus is selected from a group consisting of *Trichophyton equinum* DSM No. 7276, *Trichophyton mentagrophytes* DSM No. 7279, *Trichophyton sarkisovii* DSM No. 7278, *Trichophyton verrucosum* DSM No. 7277, *Microsporum canis DSM No.* 7281, *Microsporum canis var. obesum* DSM No. 7280, *Microsporum canis var. distortum* DSM No. 7275, *Microsporum gypseum DSM No.* 7274, and *Candida albicans* DSM No. 9565.

8. An antigenic material comprising the ASMP material obtained by a process as claimed in claim 1, and at least one material selected from the group consisting of antigenic material not soluble in aqueous solutions (AMNP) and antigenic exogenous material (AEMP).

9. The antigenic material as claimed in claim 8, wherein the antigenic material is a combination of ASMP from strain *T. mentagrophytes* DSM No. 7279, ASMP from strain *M. gypseum* DSM No. 7274, and ASMP from strain *C. albicans* DSM No. 9656.

10. The antigenic material as claimed in claim 8, wherein the antigenic material is a combination of ASMP from strain *M. gypseum* DSM No. 7274 and ASMP from strain *C. albicans* DSM No. 9656.

11. A pharmaceutical composition comprising at least one antigenic material as claimed in claim 8 in a pharmaceutically acceptable carrier.

12. The composition as claimed in claim 11, wherein the antigenic material is in a solution for injection.

13. A vaccine comprising at least one antigenic material as claimed in claim 8.

14. The vaccine as claimed in claim 13, further comprising a pharmaceutically acceptable carrier.

15. An antigenic material comprising at least one of the materials selected from a group consisting of ASMP, ANMP, and AEMP; wherein said material is obtained by a process as claimed in claim 7.

16. A pharmaceutical composition comprising at least one antigenic material obtained by a process as claimed in claim 5 in a pharmaceutically acceptable carrier.

17. A pharmaceutical composition comprising at least one antigenic material obtained by a process as claimed in claim 6 in a pharmaceutically acceptable carrier.

18. A pharmaceutical composition comprising at least one antigenic material as claimed in claim 15 in a pharmaceutically acceptable carrier.

19. A vaccine comprising at least one antigenic material obtained by a process as claimed in claim 5.

20. A vaccine comprising at least one antigenic material obtained by a process as claimed in claim 6.

21. A vaccine comprising at least one antigenic material as claimed in claim 15.

22. A vaccine that comprises antigenic material obtained by a process as claimed in claim 1.

* * * * *